US009002450B2

(12) United States Patent
Rosenberg et al.

(10) Patent No.: US 9,002,450 B2
(45) Date of Patent: Apr. 7, 2015

(54) SYSTEMS AND METHODS FOR ASSESSING THE SPHERICITY AND DIMENSIONAL EXTENT OF HEART CHAMBERS FOR USE WITH AN IMPLANTABLE MEDICAL DEVICE

(75) Inventors: Stuart Rosenberg, Castaic, CA (US); Yelena Nabutovsky, Sunnyvale, CA (US); Cecilia Qin Xi, San Jose, CA (US); Jong Gill, Valencia, CA (US); Kyungmoo Ryu, Palmdale, CA (US); Brian Jeffrey Wenzel, San Jose, CA (US); William Hsu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 622 days.

(21) Appl. No.: 12/975,085

(22) Filed: Dec. 21, 2010

(65) Prior Publication Data

US 2012/0158079 A1 Jun. 21, 2012

(51) Int. Cl.
*A61N 1/00* (2006.01)
*A61N 1/362* (2006.01)
*A61N 1/365* (2006.01)
*A61N 1/368* (2006.01)
*A61N 1/39* (2006.01)

(52) U.S. Cl.
CPC .......... *A61N 1/3627* (2013.01); *A61N 1/36521* (2013.01); *A61N 1/3684* (2013.01); *A61N 1/3686* (2013.01); *A61N 1/3962* (2013.01)

(58) Field of Classification Search
None
See application file for complete search history.

(56) References Cited

U.S. PATENT DOCUMENTS

| | | | |
|---|---|---|---|
| 5,643,338 A | 7/1997 | Bornzin et al. | |
| 6,328,699 B1 | 12/2001 | Eigler et al. | |
| 6,438,408 B1 | 8/2002 | Mulligan et al. | |
| 6,512,952 B2 | 1/2003 | Stahmann et al. | |
| 6,572,557 B2 | 6/2003 | Tchou et al. | |
| 6,628,988 B2 | 9/2003 | Kramer et al. | |
| 6,643,546 B2 | 11/2003 | Mathis et al. | |
| 6,645,153 B2 | 11/2003 | Kroll et al. | |
| 6,970,742 B2 * | 11/2005 | Mann et al. | 607/23 |
| 7,115,095 B2 | 10/2006 | Eigler et al. | |
| 7,272,436 B2 | 9/2007 | Gill et al. | |
| 2003/0055345 A1 | 3/2003 | Eigler et al. | |

(Continued)

OTHER PUBLICATIONS

Opie, Lionel H. et al., "Controversies in Cardiology 4—Controversies in ventricular remodeling," Lancet. 2006;367: 356-367.

(Continued)

*Primary Examiner* — Christopher D Koharski
*Assistant Examiner* — Elizabeth K So

(57) ABSTRACT

Techniques are provided for use with an implantable medical device for assessing left ventricular (LV) sphericity and atrial dimensional extent based on impedance measurements for the purposes of detecting and tracking heart failure and related conditions such as volume overload or mitral regurgitation. In some examples described herein, various short-axis and long-axis impedance vectors are exploited that pass through portions of the LV for the purposes of assessing LV sphericity. In other examples, impedance measurements taken along a vector between a right atrial (RA) ring electrode and an LV electrode implanted near the atrioventricular (AV) groove are exploited to assess LA extent, biatrial extent or mitral annular diameter. The assessment techniques can be employed alone or in conjunction with other heart failure detection techniques, such as those based on left atrial pressure (LAP.)

22 Claims, 17 Drawing Sheets

(56) References Cited

U.S. PATENT DOCUMENTS

| | | |
|---|---|---|
| 2006/0058588 A1 | 3/2006 | Zdeblick |
| 2007/0179390 A1 | 8/2007 | Schecter |
| 2007/0179569 A1 | 8/2007 | Zdeblick |
| 2008/0306567 A1 | 12/2008 | Park et al. |
| 2009/0262109 A1 | 10/2009 | Markowitz et al. |
| 2010/0152801 A1* | 6/2010 | Koh et al. ............... 607/9 |

OTHER PUBLICATIONS

Kono, Tatsuji MD et al., "Left Ventricular Shape as a Determinant of Functional Mitral Regurgitation in Patients with Severe Heart Failure Secondary to Either Coronary Artery Disease or Idiopathic Dilated Cardiomyopathy," Am J Cardiol. 1991;68:355-359.

* cited by examiner

SYSTEMS AND METHODS FOR ASSESSING THE SPHERICITY AND DIMENSIONAL EXTENT OF HEART CHAMBERS FOR USE WITH AN IMPLANTABLE MEDICAL DEVICE

FIELD OF THE INVENTION

The invention generally relates to implantable medical devices such as pacemakers, implantable cardioverter-defibrillators (ICDs) and cardiac resynchronization therapy (CRT) devices and, in particular, to techniques for assessing changes in the sphericity and dimensional extent of heart chambers using such devices and for detecting and trending heart failure based on the changes.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body can eventually complicate the clinical prognosis. For example, when the heart attempts to compensate for reduced cardiac output, it adds muscle causing the ventricles (particularly the left ventricle) to grow in thickness in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

In view of the potential severity of heart failure, it is important to detect the onset of the condition within a patient using implantable medical devices and to track or trend the progression thereof so that appropriate therapy can be provided. It is to this end that the invention is generally directed. More specifically, techniques are provided herein for assessing heart failure and related conditions such as volume overload and mitral regurgitation based on changes in the degree of sphericity of the left ventricle (LV) and changes in the dimensional extent of the atria.

SUMMARY OF THE INVENTION

In accordance with an exemplary embodiment of the invention, a method is provided for use with an implantable medical device for assessing changes in the sphericity and/or dimensional extent of particular heart chambers. Briefly, the device measures parameters representative of impedance (such as impedance, immittance, conductance or admittance) along selected vectors passing through portions of the heart of the patient in which the device is implanted and then determines parameters representative of heart chamber sphericity and/or atrial dimensional extent based on the impedance signals or based on parameters derived therefrom. In particular, the device assesses LV sphericity and atrial extent. LV sphericity pertains primarily to the shape of the outer wall of the LV, which can be relatively spherical or relatively ellipsoidal depending upon the condition of the heart. A relatively spherical LV is indicative of LV volume overload, heart failure and related conditions. The LV of a healthy heart is typically more ellipsoidal. Atrial dimensional extent primarily pertains to left atrial (LA) extent, biatrial extent or mitral annular diameter. In accordance with the invention, the electrodes of a multi-electrode LV lead are used to provide information regarding the shape of the heart, particularly the outer wall shape.

In this regard, impedance vectors from the right ventricular (RV) to each of several multi-electrode LV lead electrodes can be measured serially, wherein the LV electrodes are arranged along a single branch of the coronary sinus. Based on patient anatomy and other factors, such leads are typically targeted to the lateral or posterolateral branch. It may be positioned, for example, with all LV electrodes on the LV such that the distal electrode is very apical and the most proximal electrode is mid-to-base level. Alternatively, the distal electrode may be positioned more at the mid-level whereas the proximal electrode may be situated in the atrio-ventricular (AV) groove adjacent to the left atrium. With either configuration, increasing distance between RV-LV electrodes with no change in blood volume (i.e. concentric hypertrophy) typically results in slightly increased impedance, while increasing chamber volumes with no change or thinning of myocardium (i.e. dilation) typically results in slightly decreased impedance because blood has higher conductivity than myocardium. By comparing the relative impedance along multiple LV electrodes, the implanted device can thereby assess the shape of the LV. By trending serial measurements, the device can also track any progression or change in LV chamber shape/size. Since the normal shape of the LV is an ellipsoid, and a spherical shape is associated with heart failure, volume overload, and mitral regurgitation, the impedance between the RV and each of LV electrodes can be used to derive an index of sphericity, where greater sphericity is indicative of worsening heart failure. Similarly, the larger the atrial extent—assessed, for example, based on impedance measurements along a vector from an RA ring electrode to the basal LV electrode—the greater the likelihood of heart failure and related conditions.

Once the degree of LV sphericity and/or atrial extent have been assessed, the device controls various functions based on the assessment such as: generating warning signals indicating a significant change in LV sphericity or atrial extent indicative of the heart failure; controlling or adjusting pacing therapy in response to changes in chamber shape to improve cardiac performance or remodel the heart; recording diagnostic information representative of ongoing trends in sphericity or atrial extent, etc.

In an illustrative implementation, the implantable device is equipped with a lead system having, at least, an RV coil electrode and a set of relatively smaller multi-site left ventricular (multi-electrode LV) electrodes distributed along the LV from near its base to its apex. Impedance values are obtained by driving a subthreshold AC current between the RV coil and the housing of the device (also called the "can.") Separate impedance values are then measured between the RV coil and each of the LV electrodes. These impedance values are referred to herein as "short-axis" values since the vectors used to measure impedance between the RV coil and the LV electrodes are at least somewhat perpendicular to the long-axis of the ventricles. The device then detects changes, if any, in the short-axis impedance values over time and tracks progression in LV chamber shape from ellipsoid to spherical based on the changes in short-axis impedance. As noted, within a healthy heart, the outer wall of the LV is relatively ellipsoidal. With heart failure, the outer wall of the LV can become more spherical. Hence, LV sphericity can be indicative of heart failure.

In one particular example wherein the LV electrodes include an apical (distal/tip) electrode, a basal (proximal) electrode and a set of intermediate electrodes, LV sphericity is determined based on the short-axis impedances as follows. The measured short-axis impedance values from the RV coil to each of the LV electrodes are converted to distance values, based on pre-determined impedance-to-distance calibration, to assess the relative spacing between the RV coil and each of the LV electrodes. The short-axis impedance/distance values are sorted from basal to apical (herein denoted S4-S1) and then the device assesses the sphericity of the LV based on whether changes in the short-axis distances from basal to apical are substantially monotonic. This can be achieved by: detecting deviations in short-axis distances from basal to apical (e.g. by stepping from S4 to S3, S3 to S2, etc.); generating a sphericity index by incrementing/tallying points for each decrease from basal to apical and decrementing points for each increase from basal to apical; and then assessing sphericity based on the sphericity index, with a higher score indicating a relatively high degree of ellipsoidicity (i.e. healthy heart) and a lower score indicating a relatively high degree of sphericity (i.e. heart failure.) The index is tracked over time, any significant increase in LV sphericity is deemed indicative of progression of heart failure, and suitable warnings are generated for the patient and clinician. Pacing therapy or other forms of therapy can be initiated or adjusted, such as CRT.

In another example, the device additionally exploits a right atrial (RA) electrode to measure a set of "long-axis" impedance values between the RA and the various LV electrodes. These impedance values are referred to herein as "long-axis" values since the vectors used to measure impedance between the RA and the LV electrodes are at least somewhat parallel to the long-axis of the ventricles. The sphericity of the LV is then assessed by determining a ratio of short-axis impedance to long-axis impedance (or corresponding distance values) for each of the LV electrodes and then determining whether the ratios decrease monotonically from the basal electrode to the apical electrode. If there is a monotonic decrease from base to apex, the device deems that there is a relatively small degree of LV sphericity (and hence, the outer LV wall is properly ellipsoidal.) Conversely, if there is an increase or an increase followed by a decrease in the short-axis to long-axis impedance ratio, then the device concludes that there is a relatively large degree of LV sphericity indicative of heart failure. In still other examples, rather than using the RV coil and device housing to drive the impedance-measuring current, the device instead drives current between a superior vena cava (SVC) coil electrode and the LV electrodes, shorted together.

As noted, atrial dimensional extent can also be assessed. Briefly, impedance between a fixed electrode (RV septal, RV apex, or RA) and the proximal electrode of a multi-electrode LV lead can be used as a surrogate for LA dimension. The proximal LV electrode can be situated in or near the AV groove in the coronary sinus tree. Again, increased blood volumes are typically accompanied by decreased impedance. LA dilation is associated with increased left atrial pressure (LAP), which is another well-known marker of heart failure. In an illustrative example, current is driven between the RV coil and the device housing with impedance then measured from the RA ring to a basal LV electrode mounted near the AV groove. If the RA ring-basal LV impedance is relatively large, the device assesses a relatively large atrial extent. Conversely, if the RA ring-basal LV impedance is relatively small, the device assesses a relatively small atrial extent. A relatively large atrial extent is associated with heart failure and related conditions. In still other examples, the device exploits an RV electrode positioned in the RV outflow tract (RVOT) of the heart of the patient. Current is driven between a suitable coil electrode and the device housing with impedance then measured from the RVOT ring to the basal LV electrode, again mounted near the AV groove. If the RVOT ring-basal LV impedance is relatively large, the device assesses a relatively large atrial extent. Conversely, if the RVOT ring-basal LV impedance is relatively small, the device assesses a relatively small atrial extent.

In some examples, the device takes steps to confirm the detection of changes in LV sphericity or atrial extent before taking responsive action. For example, contact pressure between electrodes and patient tissue can be monitored. In one particular example, the device assesses a degree of contact pressure between electrodes and patient tissue and tracks changes, if any, in contact pressure over time while also tracking changes, if any, in LV sphericity and atrial extent. Changes in LV sphericity and atrial extent should cause corresponding changes in contact pressure as the changing shape of the heart causes heart tissues to press against the electrodes. Hence, if no such changes in contact pressure are detected, any actions to be taken by the device in response to changes in sphericity/dimensional extent are preferably deferred pending clinician review.

Although summarized with respect to examples where the implanted device performs the various procedures to assess sphericity/dimensional extent, it should be understood that an external system might additionally or alternatively be exploited. For example, impedance data collected by the implanted device can be transmitted to an external system, which analyzes the data to assess sphericity/dimensional extent. The external device can be, for example, a suitably equipped bedside monitor, device programmer or centralized processing system. In addition, it should be understood that the sphericity and dimensional extent of other heart chambers can also be assessed using the techniques described herein, assuming the implantable system is equipped with suitably positioned sets of electrodes.

In the various examples described herein, impedance measurements are used but it should be understood that related electrical parameters might be detected and/or exploited instead, such as admittance, conductance or immittance. Those skilled in the art can convert between these related parameters. Herein, "parameters representative of impedance" is deemed to include related electrical parameters such as admittance, conductance and immittance.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
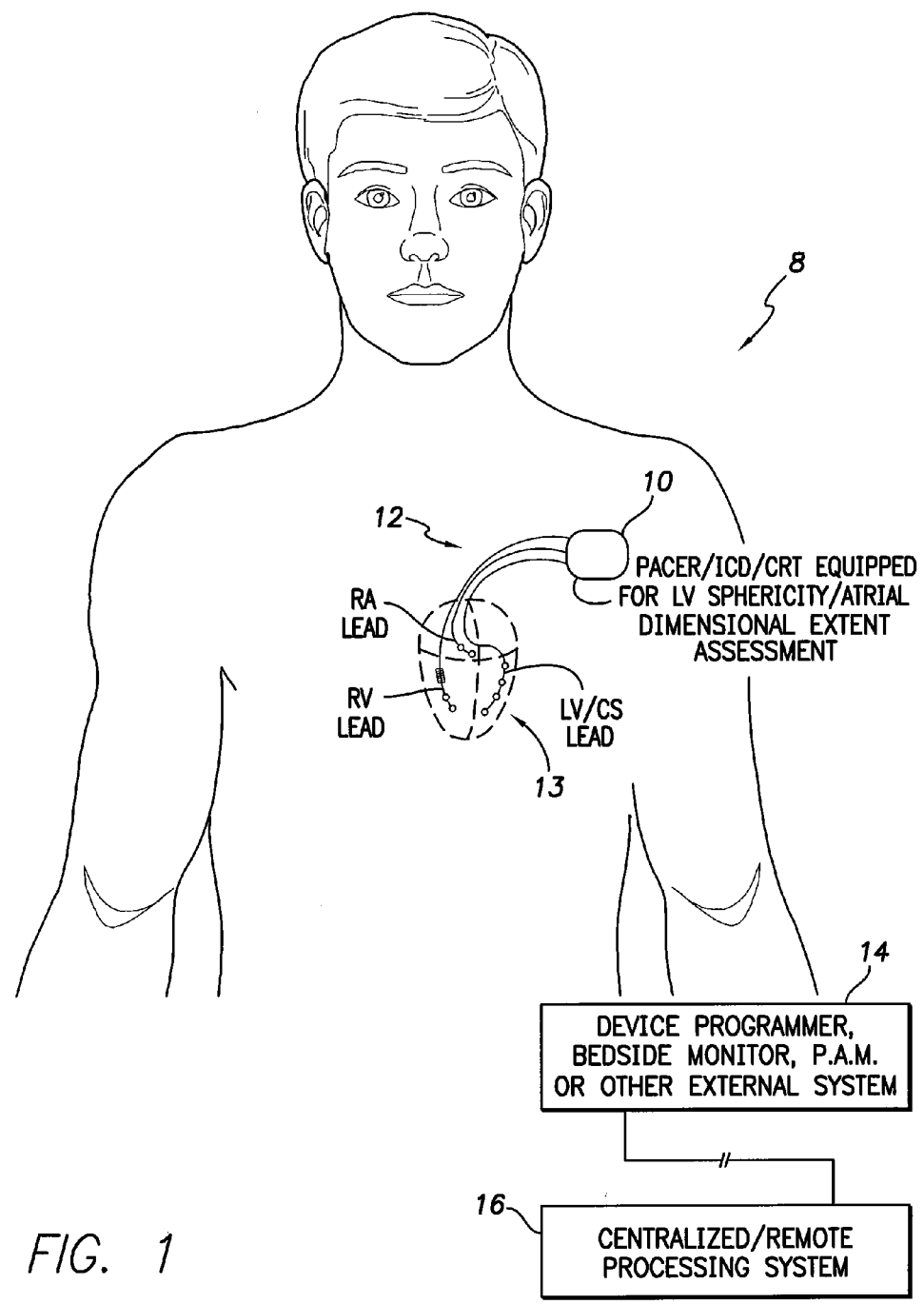
FIG. 1 illustrates pertinent components of an implantable medical system having a pacemaker, ICD or CRT device equipped to assess LV sphericity and/or atrial dimensional extent.

FIG. 1 illustrates an implantable medical system 8 equipped to assess LV sphericity and atrial dimensional extent within the heart of a patient, as well as equipped to perform numerous other functions. The medical system 8 includes a pacer/ICD/CRT 10 or other implantable cardiac stimulation device equipped with one or more cardiac sensing/pacing leads 12 implanted on or within the heart of the patient, including a multi-pole LV lead implanted via the coronary sinus (CS). To illustrate the multi-pole configuration of the LV lead, a set of LV electrodes 13 is shown distributed along the LV lead. In the examples described herein, a quadrapolar (or "quad-pole" or "quadripolar") lead is employed (such as the Quartet™ lead provided by St Jude Medical) to assess LV sphericity and atrial extent. Other suitable leads may instead be employed, including leads with more or fewer electrodes. Also, as shown, an exemplary RV lead is provided that includes an RV tip/ring electrode pair and an RV coil. An RA lead is also provided that includes an RA tip/ring pair. Other electrodes of various sizes and shapes may be additionally or alternatively provided, such as coil electrodes mounted in or on the RA or CS. See the other figures provided herein for a more complete and accurate illustration of the location of various exemplary lead systems. Although identified as a pacer/ICD/CRT in FIG. 1, it should be understood that device 10 can be any suitably equipped implantable medical device, such as a standalone pacemaker, ICD, or CRT device, including CRT-D and CRT-P devices. In the following, for brevity, device 10 will be referred to simply as a pacer/ICD.

Based in the assessment of chamber sphericity/dimensional extent, the pacer/ICD can then detect and track heart failure, LV volume overload or related conditions using techniques described below. Depending upon the particular conditions and/or parameters detected, the pacer/ICD will issue warning signals, if appropriate. For example, if significant LV volume overload is detected based on increasing LV sphericity, warning signals may be generated to warn the patient, either using an internal warning device (which can be part of the pacer/ICD) or using an external bedside monitor/handheld warning device 14 or other external system. The internal warning device may be a vibrating device or a "tickle" voltage device that, in either case, provides perceptible stimulation to the patient to alert the patient so that the patient may consult a physician. In one example, once the warning is felt, the patient positions an external warning device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this warning/notification technique, see U.S. Pat. No. 7,272,436 to Gill et al.

If a bedside monitor is provided, the bedside monitor provides audible or visual alarm signals to alert the patient or caregivers, as well as providing textual or graphic displays. In addition, any diagnostic information pertaining to the deteriorating cardiac condition of the patient is transferred to the bedside monitor or is stored within the pacer/ICD for subsequent transmission to an external programmer for review by a physician or other medical professional. The physician may then prescribe therapies to address the condition. The physician may also adjust the operation of the pacer/ICD to activate, deactivate or otherwise control any therapies that are automatically applied, including titration of medications. The bedside monitor may be directly networked with an internet network site or a centralized processing system 16 for immediately notifying the physician of any urgent medical condition. The centralized system may include such systems as Merlin.Net of St. Jude Medical, which may be used in conjunction with bedside monitors or similar devices such as the HouseCall™ remote monitoring system or the Merlin@home systems, also of St. Jude Medical.

In some implementations, the pacer/ICD itself performs the sphericity and dimensional extent assessment based on impedance measurements made using its leads. In other implementations, the device transmits the impedance measurements to the external system 14, which performs the assessment. In the following examples, it is assumed that the pacer/ICD performs the assessment using on-board components. An example where the external programmer performs the assessment described below with reference to FIG. 16.

Hence, FIG. 1 provides an overview of an implantable medical system for assessing LV sphericity and atrial dimension and for delivering appropriate warning/notification signals and therapy, if needed. Embodiments may be implemented that do not necessarily perform all of these functions. For example, embodiments may be implemented that assess sphericity/dimensional extent but do not automatically initiate or adjust therapy. In addition, note that the particular locations of the implanted components shown in FIG. 1 are merely illustrative and may not necessarily correspond to actual implant locations. Also, the descriptions below uses the Quartet™ lead as an exemplary component of the invention, though it should be understood that any suitable multielectrode lead could instead be used for LV sphericity assessment and that any electrode near the AV groove, LA, or mitral annular plane (for example on bipolar lead) can also be used for the LA dimension assessment.

Overview of Sphericity and Dimensional Extent Assessment Techniques

Figure 2:
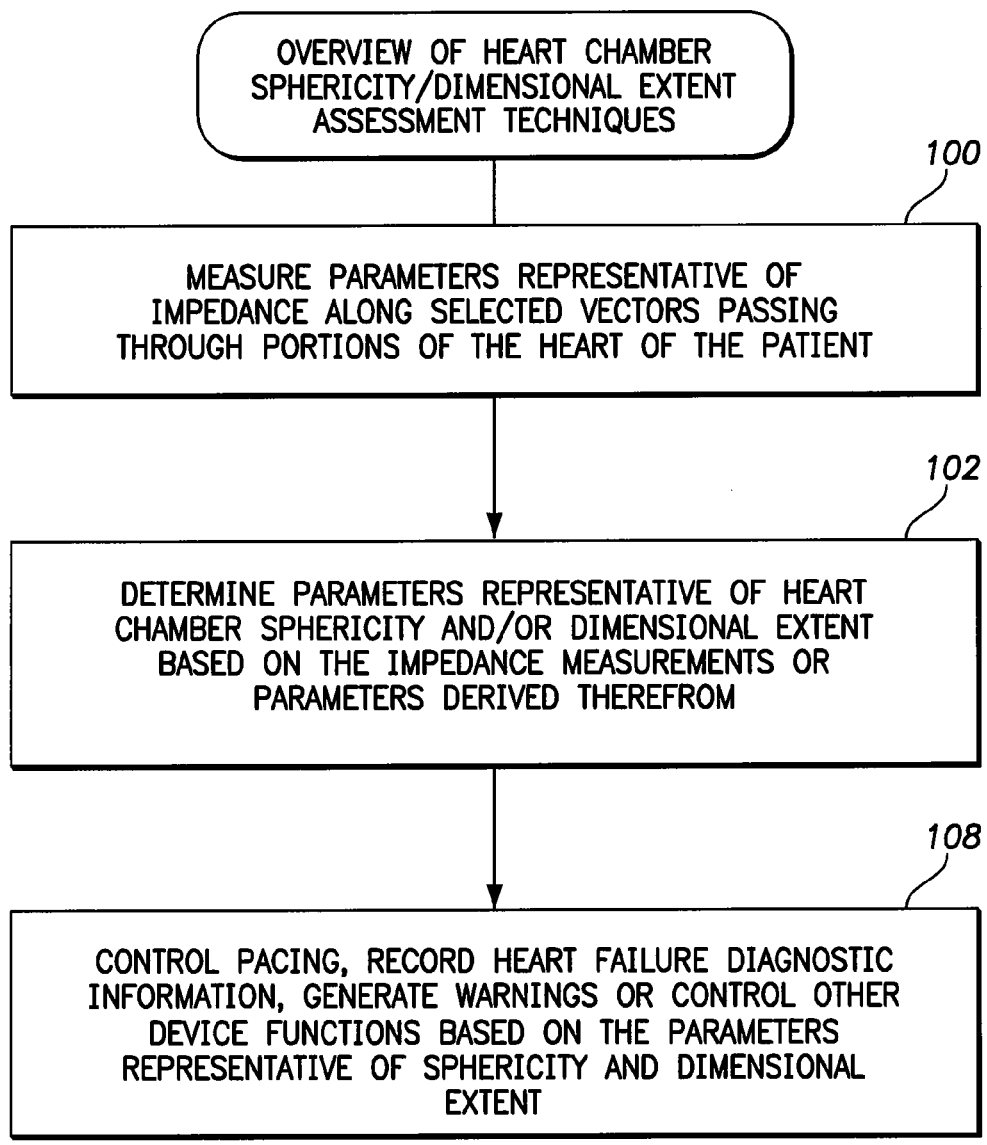
FIG. 2 provides an overview of techniques to assess LV sphericity and/or atrial extent based on impedance measurements, which may be performed by the system of FIG. 1.
Figure 3:
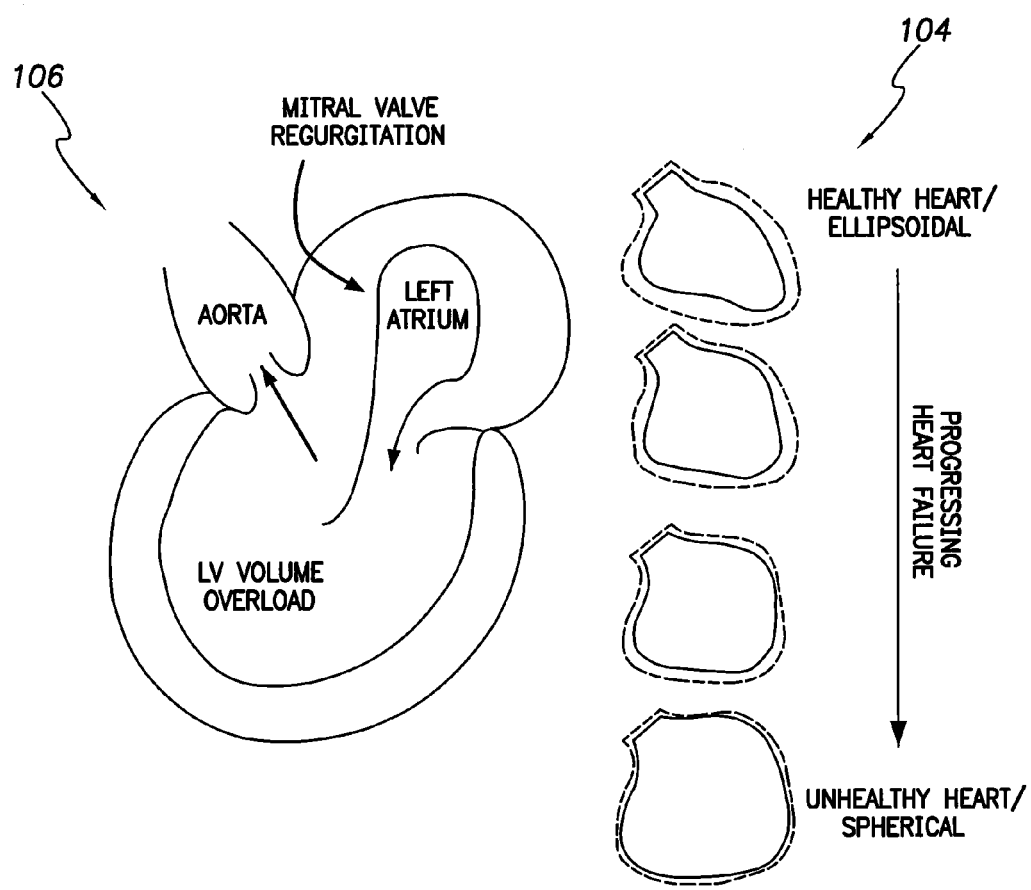
FIG. 3 graphically illustrates changes in the shape of heart detected by the technique of FIG. 2 during heart failure and LV volume overload that cause the LV to become more spherical.

FIGS. 2 and 3 broadly summarize techniques that may be exploited by the implantable device of FIG. 1 (or other suitably equipped devices) for assessing LV sphericity, atrial extent, or both. Beginning at step 100 of FIG. 2, the pacer/ICD measures parameters representative of impedance (such as immittance, conductance, admittance or impedance) along selected vectors passing through portions of the heart of the patient using a set of leads. In the examples described below, various short-axis and long-axis impedance vectors are exploited that pass through portions of the LV for the purposes of assessing LV sphericity. In alternative examples, other vectors might instead be used to assess the sphericity or dimensional extent of other heart chambers. At step 102, the pacer/ICD determines parameters representative of ventricular chamber sphericity and/or atrial dimensional extent based on the impedance measurements or parameters derived therefrom, such as inter-electrode distance or displacement estimates.

Referring to FIG. 3, the sphericity of the heart is illustrated. More specifically, a series of heart diagrams 104 show the increasing sphericity that can result from LV volume overload due to heart failure. The healthy heart is relatively ellipsoidal rather than spherical. In particular, the outer walls of the ventricles of the healthy heart are relatively ellipsoidal rather than spherical. As LV volume overload increases due to long-term ischemic burden or other factors related to heart failure, the outer walls of the LV can become increasingly spherical.

See, also, heart diagram 106, which illustrates LV volume overload and associated mitral regurgitation (MR) into the LA that can arise due to heart failure. In addition to LV volume overload, LV filling pressures can be elevated by heart failure as well. This can contribute to acute pulmonary edema and decompensated heart failure in which the body tissues and even the myocardium do not receive sufficient oxygen and nutrients from the blood. Moreover, elevated ventricular filling pressures can lead to increased pressure back through the circulatory system, causing systemic circulatory problems. Still further, since the atrium is a thin-walled structure, elevated pressures can lead to left atrial stretch and, over time, to a remodeling or dilation of the LA, including an increase in atrial extent, as represented by LA extent, biatrial extent or mitral annular diameter. The capability of the implanted device to measure changes in sphericity and/or dimensional extent associated with worsening heart failure helps the device more accurately detect and predict decompensation events, alone or in combination with other heart failure detection techniques.

Returning to FIG. 2, at step 108, having assessed or determined chamber sphericity/dimensional extent, the pacer/ICD then controls pacing, records heart failure diagnostic information, generates warnings or controls other device functions based on the parameters representative of sphericity and/or atrial extent (or on any parameters derived therefrom.) That is, the pacer/ICD controls one or more device functions in response to the assessment sphericity/dimensional extent. It should be understood that any function that the pacer/ICD can perform or control, alone or in combination with other devices, is a "device function." This includes but is not limited to: detecting medical conditions such a heart failure, MR or LV volume overload and tracking and trending those conditions; controlling pacing or other forms of therapy; generating, recording and transmitting diagnostic information; generating warnings for the patient or clinician; etc.

An advantage of the techniques described herein is that, unlike some prior art heart failure detection techniques that do not exploit sphericity/dimensional extent, the techniques described herein are fairly specific to heart failure and related conditions so as that the pacer/ICD can avoid significant false alarms without missing true heart failure events. In particular, the shape and dimensional information provided can be useful in guiding LV remodeling. These techniques can be exploited in connection with other heart failure detection techniques, such as those that detect fluid accumulations. In particular, by measuring impedance in relation to cardiac geometry, confidence is raised that any detected fluid accumulation is due to worsening heart failure rather than extra-cardiac causes. Note also that the sphericity/dimensional extent assessment techniques described herein can be used as one input into a multi-sensor algorithm for trending heart failure status, along with other input derived from CI (cardiogenic impedance), AV/VV timing, ER (evoked response) or PE (pulmonary edema) impedance.

Turning now to FIGS. 4-13, various exemplary embodiments will be described in detail for assessing LV sphericity, atrial dimensional extent or both. Individual pacer/ICDs can be equipped to implement any or all of these techniques. Depending upon the implementation, the results of different assessment techniques can be combined to enhance the reliability and accuracy of the overall assessment.

Mean Short-Axis Impedance-Based LV Sphericity Assessment

Figure 4:
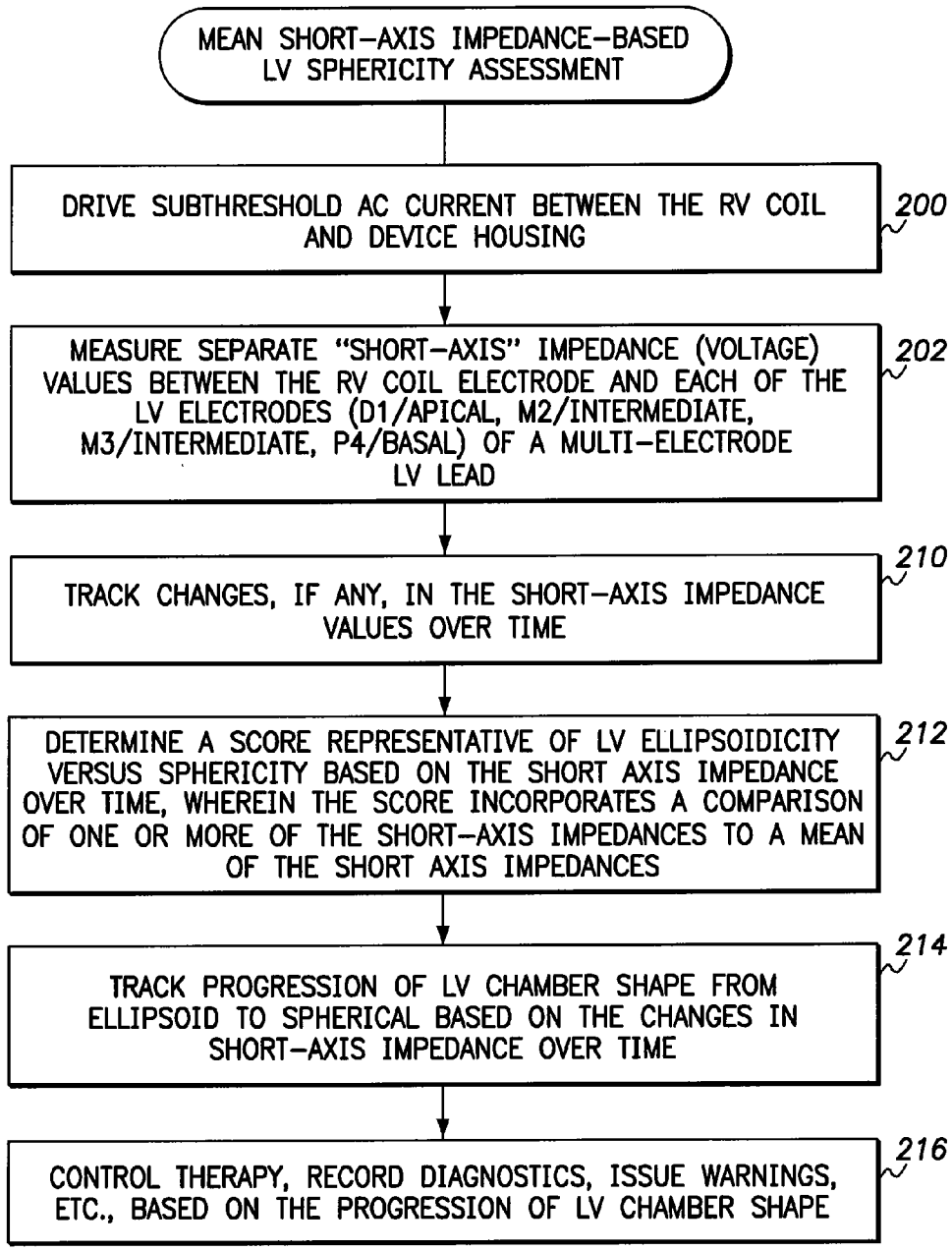
FIG. 4 is a flowchart illustrating a first exemplary implementation of the technique of FIG. 2 for assessing LV sphericity, wherein the mean of short-axis impedance values is exploited.
Figure 5:
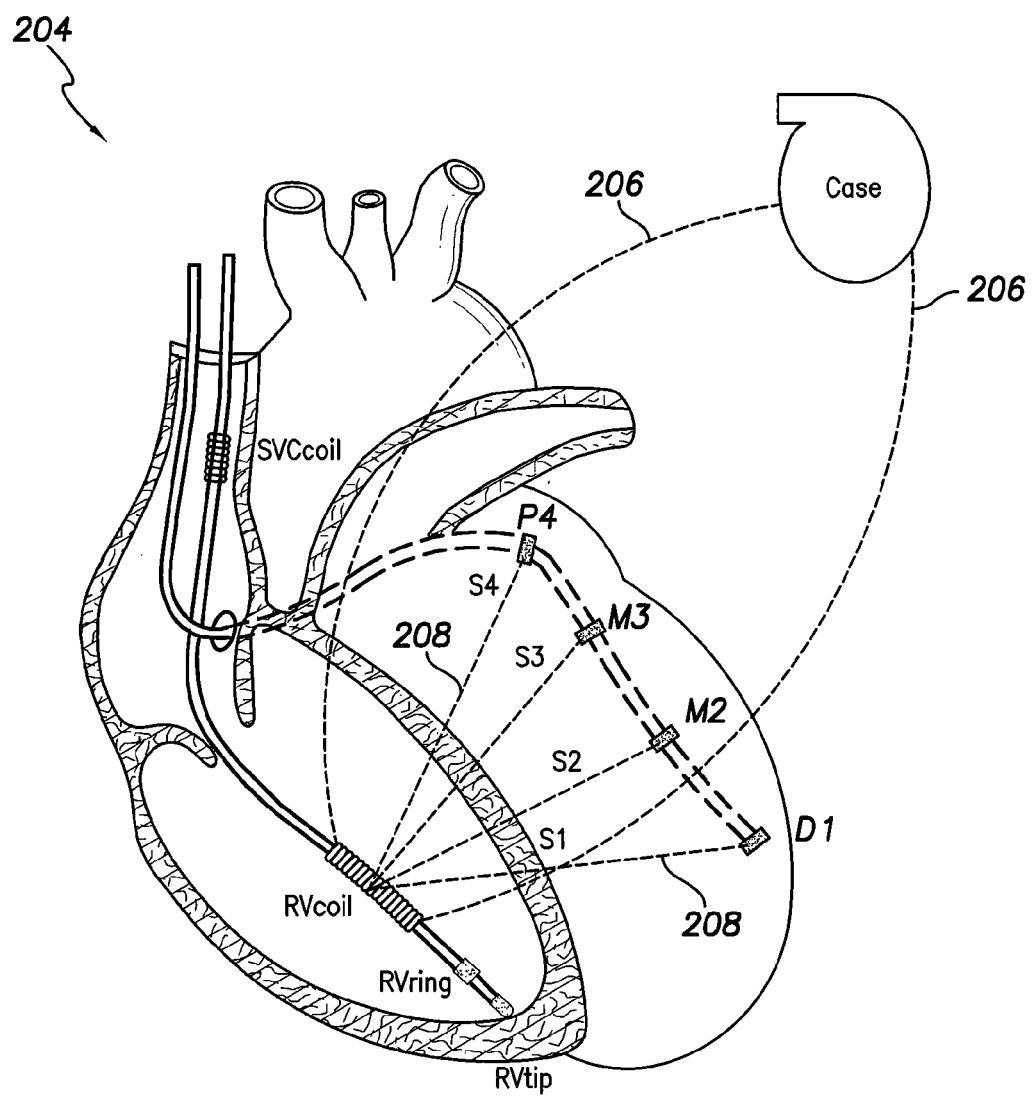
FIG. 5 illustrates the arrangement of electrodes exploited by the technique of FIG. 4 and various exemplary short-axis impedance vectors.

FIGS. 4 and 5 illustrate techniques that assess LV sphericity using short-axis impedance vectors wherein a sphericity score is generated based on a comparison of individual short-axis impedance vectors against the mean. Beginning at step 200 of FIG. 4, the pacer/ICD drives a subthreshold alternating current (AC) between the RV coil and the device-housing electrode for the purposes of measuring short-axis impedances between the RV coil and the individual LV electrodes. That is, the vector along which current is driven is different from the vectors along which impedance is measured. Both the RV coil and the device housing represent relatively large electrodes, which provide a relatively uniform current field near the measurement electrodes (i.e. the LV electrodes.) That is, it is advantageous to drive current between large electrodes that are spaced relatively far apart so that the measurement electrodes lie within a region of relatively uniform electric field. In this manner, changes in measured voltage (used to derive conductance or impedance) can be interpreted more closely as dimension or position within the field and are less perturbed by local effects.

At step 202, the device measures separate short-axis impedance values between the RV coil electrode and each of the four LV electrodes of an exemplary quadrapole lead, which are denoted herein as D1/apical, M2/intermediate, M3/intermediate, and P4/basal. (The "quad-pole" lead is, of course, just one example. Other leads may be used. In general, providing more electrodes along the LV lead provides for greater detection resolution.) A voltage drop between the RV coil electrode and each of the respective LV electrodes is detected and converted to impedance for use as a surrogate for short-axis LV length. FIG. 5 illustrates the D1, M2, M3, and P4 LV electrodes as well as the RV coil by way of heart diagram 204. The wide driving current vector between RV coil and the device housing is shown by way of broadly separated lines 206. The individual short-axis impedance measurement vectors (S1-S4) are shown by way of lines 208.

Impedance is computed by Ohm's law, but since there is AC current and the tissues through which the current travels have complex properties, there may be real (resistive) and imaginary (capacitive and/or inductive) components of the impedance. Two general types of impedance measurements are typically made by the pacer/ICD by filtering a raw signal to capture different types of information. A "pulmonary edema" (PE) impedance is implemented by taking the average resistance over a long time, such as sixteen seconds. This impedance value is referred to as "PE impedance" since it can be used to assess PE in the patient, particularly if the PE impedance vector is a transthoracic vector that crosses the lungs (such as a vector extending from the heart to the device housing.) A "cardiogenic impedance" (CI) vector is sampled much more frequently, for example at 128 Hz for 20 seconds, after gating to the refractory period, to generate a waveform representing the time course of impedance over several cardiac cycles. This impedance value is referred to as "CI impedance" since it can be used to assess the beating of the heart and related cardiogenic properties, particularly if the CI impedance vector is an intracardiac vector (such as a vector extending from the RV tip to the D1 electrode.)

Further with regard to filtering, a mean or extremely low-pass filtered version (i.e. near DC component) of CI provides an impedance component $Z0$, which is expected to be approximately equal to PE for a given set of electrode drive and measure pairs. A bandpass of approximately 0.06-0.7 Hz yields an impedance component $Zr$ that relates to respiration. A higher bandpass filtered version of CI from 0.55-64 Hz yields an impedance component $Zc$, which provides the "cardiac" component related to the beating of the heart and the flow of blood. It may also be of interest to detect and analyze a signal sampled up to 512 Hz and filtered from 0.1-50 or 0.1-150 Hz, which may relate to not only heartbeat and blood flow but also to myocardial thickening and vibrations. The sampling frequency and filter bands given here are illustrative; other ranges could be implemented to allow different components of the signal through to a given channel.

The PE or $Z0$ band is typically the easiest to interpret. For a fixed-volume medium of given conductivity, moving the measurement electrodes further apart will increase the impedance. On the other hand, if the distance remains constant but the conductivity drops, then the impedance is increased. While it can sometimes be difficult to separate these two opposing effects in the case of chamber dilation (i.e. as the cardiac volume, e.g., end diastolic volume, increases, there is more blood which increases net conductivity, but the chamber diameter is longer thereby increasing the distance between opposing electrodes), the ratios of two or more impedance vectors crossing the chamber can compensate for conductivity.

Also valuable (in addition to $Z0$) are measurements of the maximum value over a cardiac cycle, the minimum value over a cardiac cycle, and/or the peak-to-trough difference over a cardiac cycle, each of the $Zc$ (cardiac component of impedance) signal. Alternately, any of these quantities may be normalized by the $Z0$ value. These measures can be interpreted not as a chamber dimension but rather as an index of contractile state. In the pathologic course of increasing volume and sphericity, the myocardium performs less effectively and one would expect the extent of excursion over a cardiac cycle to be decreased. It is noted that methods described in the following are illustrated using the $Z0$ quantity as the measurement of interest. Interpretations of peak $Zc$ follow the same rationale with the opposite direction as $Z0$: for increasing chamber dimension and sphericity, $Z0$ would increase but (normalized or non-normalized) peak $Zc$ would decrease.

Thus, in the method of FIGS. 4 and 5, current is driven between RV coil and case and then voltage is measured between RV coil and each of P4, M3, M2, and D1. The voltage measurement is used to compute conductance or impedance by Ohm's law. Each impedance value is stored and similar measurements are taken at regular intervals, for example once per day. At step 210, the long-term trend of impedances is followed or tracked for each measurement vector. At step 212, a score is determined that is representative of LV "ellipsoidicity versus sphericity" based on the short-axis impedances over time, wherein the score incorporates a comparison of one or more of the short axis impedances to a mean of the short axis impedances. In one example, the short-axis impedance from RV coil to M2 (i.e. slice S2) can be compared against the mean of all four short-axis impedances. If the S2 impedance increases relative to the mean, the device interprets that as being indicative of an increase in sphericity. In other examples, the short-axis impedance from RV coil to M3 (i.e. slice S3) is instead used, or some combination of both S2 and S3.

As another example, the progression of sphericity can be determined by the impedance increase across the RV coil-to-M3 and RV coil-to-M2 vectors in comparison with that across the RV coil-to-P4 and RV coil-to-D1 vectors: the more the mid-level electrodes expand outward in comparison with more apical and basal electrodes, the more spherical the LV chamber and the worse the heart failure progression. Also, an index of LV sphericity can be derived by comparing segmental lengths from septum to lateral wall. These lengths can be approximated by conductance method (conductance=1/impedance). The impedance can generally be either low-frequency-content or higher-frequency-content (similar to cardiogenic impedance but with the ability to separate various frequency bands corresponding to "cardiac," "respiratory," and "mean/offset.")

At step 214, the device tracks progression of LV chamber shape from ellipsoid to spherical based on the changes in short-axis impedance over time by, for example, tracking changes in the aforementioned score. At step 216, the pacer/ICD can then controls responsive therapy, records diagnostics, issues warnings, etc., based on the progression of LV chamber shape. As already noted, a significant increase in sphericity can be indicative of heart failure, LV volume overload, MR, etc., for which prompt intervention might be required. The actions taken by the pacer/ICD will depend on device programming. In many cases, the supervising clinician will program the device to record diagnostics and issue warnings and/or also automatically adjust therapy.

In cases where the device is programmed to automatically control therapy, one type of therapy that can be automatically adjusted is CRT. Briefly, CRT seeks to normalize the dyssynchronous cardiac electrical activation and resultant dyssynchronous contractions associated with congestive heart failure by delivering synchronized pacing stimulus to both sides of the ventricles using LV and RV leads. The stimulus is synchronized to improve overall cardiac function. This may have the additional beneficial effect of reducing the susceptibility to life-threatening tachyarrhythmias. CRT and related therapies are discussed in, for example, U.S. Pat. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing". See, also, U.S. Patent Application No. 2008/0306567 of Park et al., entitled "System and Method for Improving CRT Response and Identifying Potential Non-Responders to CRT Therapy" and U.S. Patent Application No. 2007/0179390 of Schecter, entitled "Global Cardiac Performance."

Differential Short-Axis Impedance-Based LV Sphericity Assessment

Figure 6:
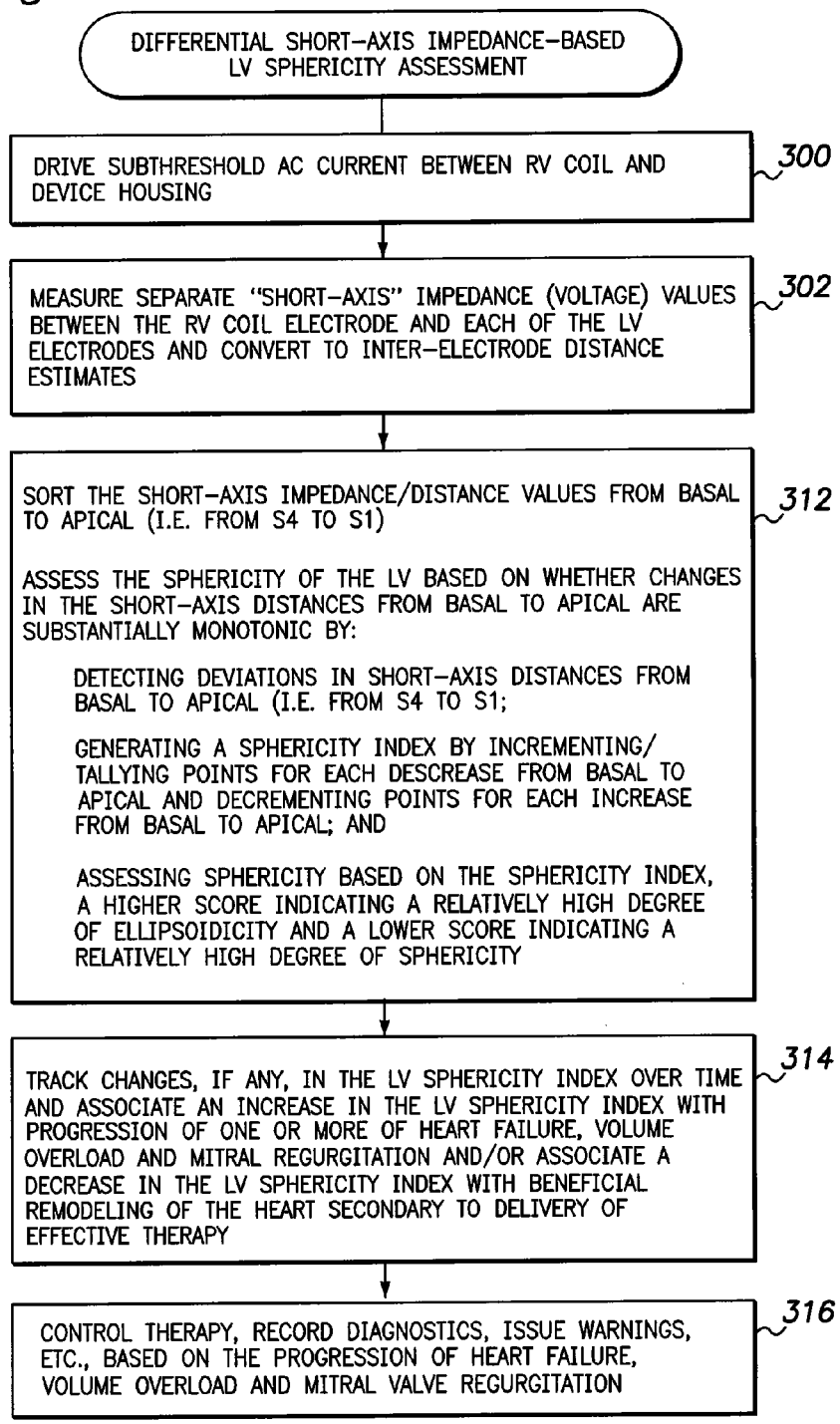
FIG. 6 is a flowchart illustrating a second exemplary implementation of the technique of FIG. 2 for assessing LV sphericity, which also employs short-axis impedance values.
Figure 7:
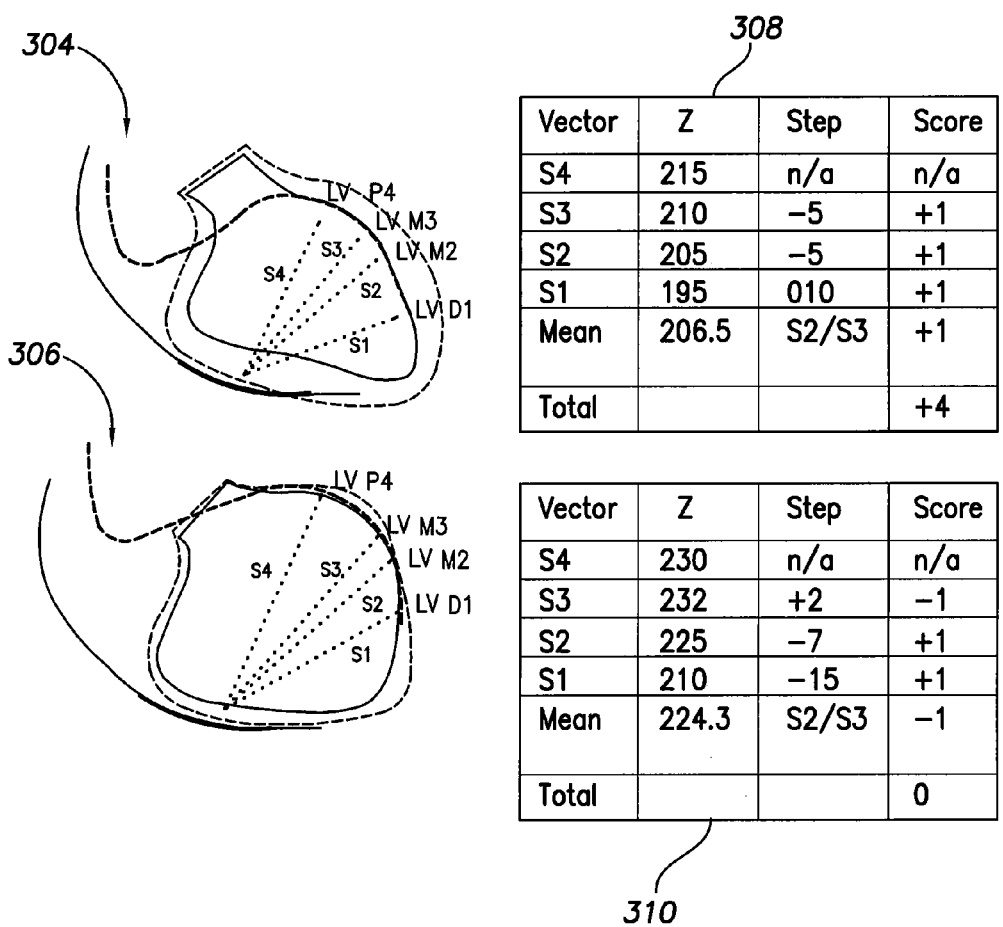
FIG. 7 illustrates the arrangement of electrodes exploited by the technique of FIG. 6 along with tables illustrating exemplary short-axis impedance values and resulting sphericity "scores"

FIGS. 6 and 7 illustrate techniques that assess LV sphericity using short-axis impedance based on differentials among distance values derived from the impedance measurements. Beginning at step 300 of FIG. 6, the pacer/ICD again drives an AC between the RV coil and the device-housing electrode for measuring short-axis impedances between the RV coil and the individual LV electrodes using the same arrangement as in FIG. 5. At step 302, the short-axis impedance values are measured along slices S1-S4 and then the measured impedance values are converted, in at least some implementations, into corresponding distance values representative of the distance from the RV coil to the respective LV electrodes. This may be achieved using pre-calibrated conversion factors that convert an impedance measurement into a distance value based on the various considerations discussed above. (See, also, FIG. 13.) Note that it is not necessary for the device to convert impedance measurements to distance values since the sphericity assessment can be based directly on the impedance values but, for understanding the invention, it is helpful to visualize the impedance values in terms of the corresponding distances separating the physical locations of the electrodes.

In a typical positioning of the LV lead in the ellipsoidal heart, it is expected that the S4 length is longest (i.e. the base has the longest "diameter") and that lengths S3, S2, and S1 will monotonically decrease. In one example of a sphericity index, a tally of +1 point is given for each decrease of impedance/distance when stepping from S4 to S3, S3 to S2, and S2 to S1; a tally of +/−0 points is given if distances are equal (within a specified tolerance), and a tally of −1 point is given for each increase of distance. Thus, by comparing each neighboring pair of short-axis slice impedances/distances, a maximum of +3 points (for strictly decreasing impedance or length from base to apex) and a minimum of −3 points (for strictly increasing impedance or length from base to apex) are possible. Next, the mean of the four impedances/distances is taken, and +1 point is given if S2 and S3 fall on opposite sides of the mean, while −1 point is tallied if S2 and S3 fall on the same side of the mean. Thus, the overall score (index) is +4 if the chamber has the proper "ellipsoid" shape; a proposed cutoff of <0 or <+1 instead indicates an abnormally spherical LV chamber; the minimum possible score is −4, which would correspond to severe apical ballooning (i.e. Tako-Tsubo syndrome).

FIG. 7 illustrates the foregoing sphericity assessment for a healthy (and relatively elliptical) heart 304 and an unhealthy (and relatively spherical) heart 306. Table 308 provides exemplary impedance values, step values and scores for heart 304. Table 308 provides exemplary impedance values, step values and scores for heart 306. Note that it may be beneficial to assign the scores for each slice, based not on a strict increasing versus decreasing, but rather only if the increase or decrease is sufficiently large. For example, a change in impedance of 2 ohms may be inconsequential and thus score 0, while a change in impedance of 20 ohms is deemed relevant and receives a score of −1. Further, it may be desirable to have graded scores, such that larger changes are tallied by more points: for example, 10 ohms is scored −1; whereas 20 ohms is scored −2.

Returning to FIG. 6, the assessment of LV sphericity made by the pacer/ICD based on the foregoing procedures is summarized by way of steps 312 and 314 wherein the device sorts the short-axis impedance/distance values from basal to apical (i.e. from S4 to S1) and then assesses the sphericity of the LV based on whether changes in the short-axis distances from basal to apical are substantially monotonic by: detecting deviations in short-axis distances from basal to apical (i.e. from S4 to S1); generating a sphericity index by incrementing/tallying points for each decrease from basal to apical and decrementing points for each increase from basal to apical; and assessing sphericity based on the sphericity index, a higher score indicating a relatively high degree of ellipsoidicity and a lower chore indicating a relatively high degree of sphericity. At step 314, the device tracks the LV sphericity index over time and associates an increase in the in the index with progression of one or more of heart failure, volume overload and mitral regurgitation. Additionally or alternatively, the device can associate a decrease in the LV sphericity index with beneficial or desirable remodeling of the heart secondary to delivery of effective therapy. For a well-shaped heart, the index value will be high, +3 or +4. Patients implanted with CRT-D or CRT-P devices will likely begin with lower index values as their hearts will already be remodeled. During progressive adverse remodeling, the index value will likely drop, while during reverse remodeling secondary to successful therapy, the index will likely increase. During concentric hypertrophy or pure dilation, the index value may remain the same while the mean of the short-axis slices will increase. Indeed, a typical time course of progressively worsening heart failure would be expected to begin with increased mean, then continue with both increasing mean and decreasing sphericity index value. Tracking not only the difference but also the ratio of impedances across various vectors can be beneficial. For example, rather than or in addition to the difference between S4-S3 impedances, the ratio of S4/S3 provides useful information. Negative "steps" can be interpreted as ratios less than 1, while positive steps are ratios greater than 1. The ratio of each short-axis slice to each other short-axis slice can be taken, i.e., not limiting to adjacent slices.

Note that due to varying placement of the LV lead and patient-specific anatomy, the choice of which vectors lengthening versus shortening to indicate increasing sphericity may vary. For this basic method, as well as the subsequent exemplary methods, differential changes may take place in any order. A clinician with knowledge of the individualized factors such as electrode location with respect to patient anatomy may use his or her judgment to assess how best to interpret the changes or ratios of impedance for a particular patient to program the operation of the device accordingly. In other words, the procedure to compute the sphericity index can be tuned to account for patient-specific differences.

At step 316, the pacer/ICD controls therapy, records diagnostics, issue warnings, etc., based on the progression of the conditions, as already discussed. In this regard, an assignment or diagnosis of "spherical LV" or alternately a change in sphericity of a certain magnitude or at a certain rate may be used guide clinical decisions. For example, the sphericity index can be configured to issue a patient alert or a physician notification when its value or rate of change crosses a threshold. Alternately, the value or rate of change of the sphericity index can be input into a multi-sensor algorithm that determines a degree of heart failure based in part on chamber shape and dimension. Outcomes of an alert or algorithm may be titration of medical regimen, changes in CRT parameters, or other interventions.

Differential Short-Axis/Long-Axis Impedance-Based LV Sphericity Assessment

Figure 8:
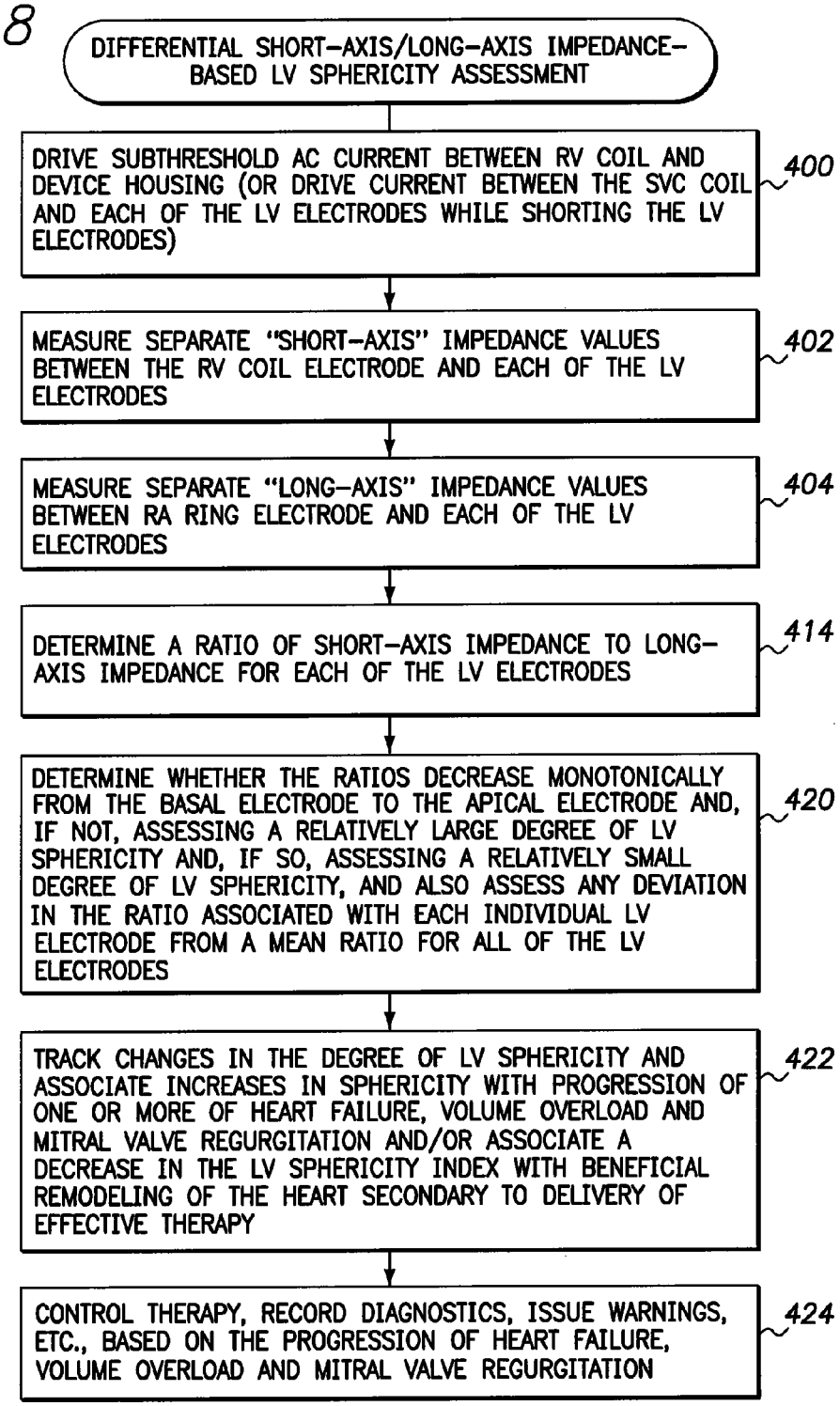
FIG. 8 is a flowchart illustrating a third exemplary implementation of the technique of FIG. 2 for assessing LV sphericity, wherein long-axis impedance values are additionally exploited.
Figure 9:
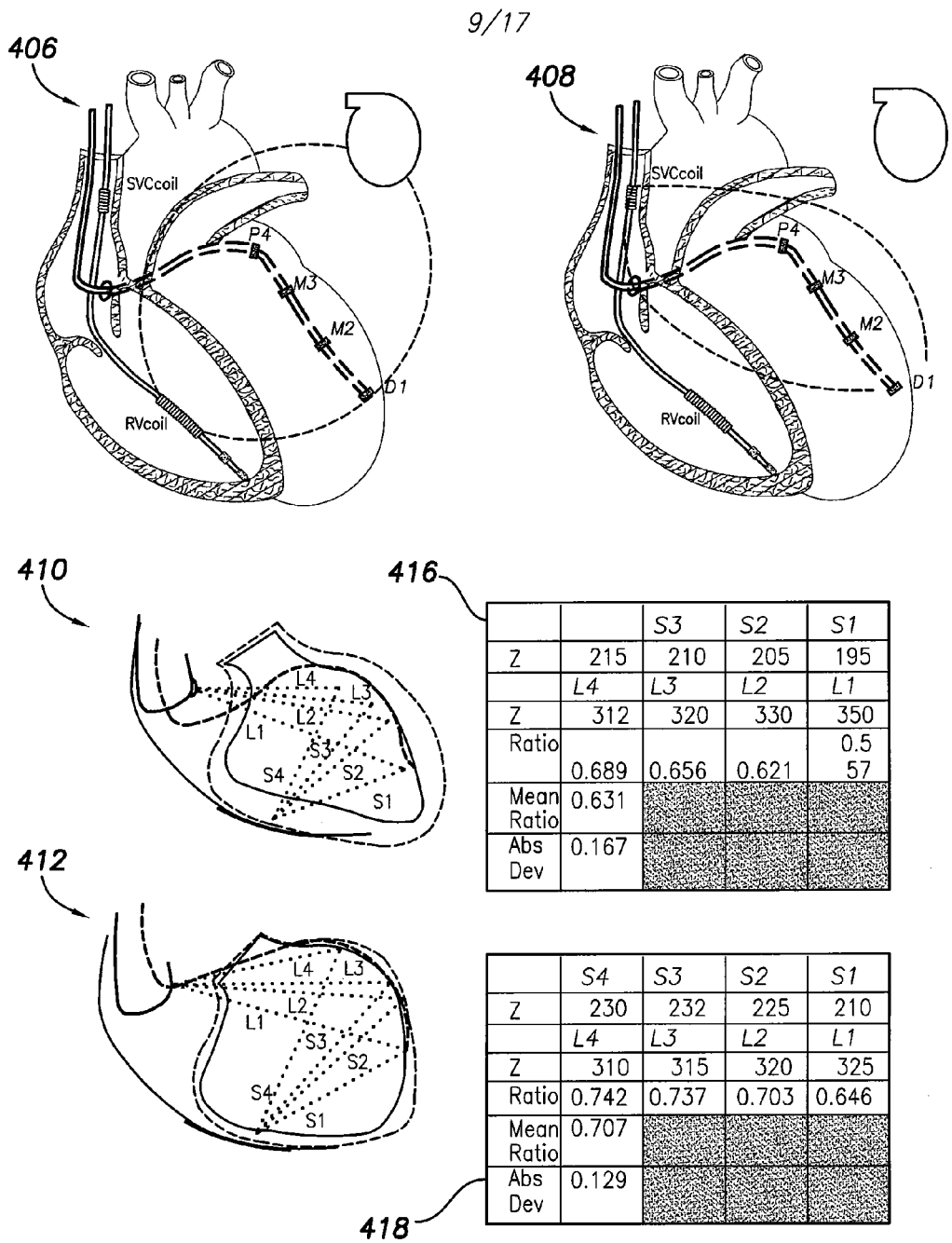
FIG. 9 illustrates the arrangement of electrodes exploited by the technique of FIG. 8 and the various short-axis and long-axis impedance vectors that are used, along with tables illustrating exemplary impedance values and pertinent ratios.

FIGS. 8 and 9 illustrate techniques that assess LV sphericity using both short-axis and long-axis impedance vectors. Beginning at step 400 of FIG. 8, the device drives an AC between the RV coil and the device-housing electrode for measuring short-axis impedances between the RV coil and the individual LV electrodes and also for measuring long-axis impedances between the RA tip electrode and the LV electrodes. Alternatively, current can be driven between the SVC coil and the LV electrodes, shorted together. This makes an "effective" electrode that is much larger than each LV electrode alone. At step 402, short-axis impedance values are then measured along slices S1-S4. At step 404, long-axis impedance values are measured between the RA ring electrode and each of the LV electrodes. That is, a voltage drop between the RA ring and each of the respective LV electrodes is detected and converted to impedance for use as a surrogate for long-axis LV length.

FIG. 9 illustrates the two exemplary current vectors (RV coil-case and SVC coil-multi-electrode LV) by way of heart diagrams 406 and 408. The short-axis and long-axis vectors or slices are shown via heart diagrams 410 and 412, where heart 410 is healthy and relatively elliptical and heart 412 is more spherical due to heart failure. Note that the long-axis vectors are denoted L1-L4.

Returning to FIG. 8, the device then determines a ratio of short-axis impedance to long-axis impedance for each of the LV electrodes. The basal electrode (P4) should have the largest short-axis and the smallest long-axis, while the apical electrode (D1) should have the largest long-axis and the smallest short-axis, in a healthy ellipsoidal heart. Thus, it is expected that when stepping from the S4/L4 ratio to S3/L3, S2/L2, and S1/L1, the value of the ratio progressively decreases. Further, the more ellipsoidal (normal shaped) the heart, the higher the sum of absolute deviations between each ratio and the mean of ratios. On the other hand, a more rounded or spherical heart would have non-monotonic progression of ratio values from S4/L4 through S1/L1, and each ratio would be closer to the mean of the ratios. Thus, the sum of absolute deviations of each individual short/long-axis slice ratio from the mean of the ratios [(S4/L4+S3/L3+S2/L2+S1/L1)/4] provides an index of sphericity, where a perfect sphere would have index of zero and increasing values of the index correspond to progressively longer ellipsoids.

Exemplary ratio impedance values, ratio values, etc., are shown in FIG. 9 within tables 416 and 418. In other examples, a sphericity index may be derived using only the long-axis slices, or taking into account the physical electrode spacing and size on the LV lead and those used to drive and measure current. The examples provided herein are the presently contemplated preferred embodiments. (It is noted that at least some ratio-based sphericity indices of the prior art have used more complicated formulae to quantify sphericity, such as sphericity=(end diastolic volume)/((long-axis dimension$^3$)*$\pi$/6.)) This formula is echo-based, i.e. it uses actual axis lengths and/or volumes derived from echocardiography rather than impedance-derived estimates or surrogates of axis length.

The assessment of LV sphericity made by the pacer/ICD based on the foregoing procedures is summarized by way of steps 420 and 422, wherein the device determines whether the ratios decrease monotonically from the apical electrodes to the basal electrodes and, if not, the device assesses a relatively large degree of LV sphericity and, if so, the device assesses a relatively small degree of LV sphericity. Additionally, the device can assess any deviation in the ratio associated with each individual LV electrodes from a mean ratio for all of the LV electrodes. As noted, the sum of absolute deviations of each individual short/long-axis slice ratio from the mean of the ratios can also provide an index of sphericity. At step 422, the pacer/ICD tracks changes in the degree of LV sphericity and associate increases in sphericity with progression of one or more of heart failure, volume overload and mitral valve regurgitation. Additionally or alternatively, as already noted, the device can associate a decrease in the LV sphericity index with beneficial or desirable remodeling of the heart secondary to delivery of effective. At step 412, the device controls therapy, records diagnostics, issue warnings, etc., based on the progression of heart failure, volume overload and MR, as already discussed.

As an alternative long-axis slice measurement, a shock coil on the CS lead (see FIG. 14) can be used as one electrode. Both the current drive and voltage measure, for example, may occur between the CS coil and each of the LV electrodes, or drive current from CS coil to all LV electrodes plus RV tip and RV ring shorted together can be used, within measurement from each LV electrode to the CS coil. Further, driving current from the SVC coil to all LV electrodes and measuring voltage between each LV electrode and CS coil would also be a desirable configuration.

Note also that any of the aforementioned sphericity indices can be input to a multivariate index of overall heart failure progression, which incorporates other heart failure detection techniques. Other techniques for assessing or corroborating heart failure and related conditions are discussed in the following documents: U.S. Pat. No. 6,328,699 to Eigler, et al., entitled "Permanently Implantable System and Method for Detecting, Diagnosing and Treating Congestive Heart Failure"; U.S. Pat. No. 6,970,742 to Mann, et al., entitle "Method for Detecting, Diagnosing, and Treating Cardiovascular Disease"; U.S. Pat. No. 7,115,095 to Eigler, et al., entitled "Systems and Methods for Detecting, Diagnosing and Treating Congestive Heart Failure"; U.S. patent application Ser. No. 11/100,008, of Kil et al., entitled "System and Method for Detecting Heart Failure and Pulmonary Edema based on Ventricular End-Diastolic Pressure using an Implantable Medical Device", filed Apr. 5, 2005; U.S. patent application Ser. No. 11/014,276, of Min et al., entitled "System and Method for Predicting Heart Failure based on Ventricular End-Diastolic Volume/Pressure using an Implantable Medical Device", filed Dec. 15, 2004; U.S. patent application Ser. No. 10/810,437, of Bomzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac Stimulation Device," filed Jan. 17, 2003. See also: U.S. Pat. No. 6,572,557, to Tchou, et al.; U.S. Pat. No. 6,645,153, to Kroll et al., entitled "System and Method for Evaluating Risk of Mortality Due To Congestive Heart Failure Using Physiologic Sensors", and U.S. Pat. No. 6,438,408 to Mulligan et al., entitled "Implantable Medical Device for Monitoring Congestive Heart Failure."

Impedance-Based Atrial Dimensional Extent Assessment

Figure 10:
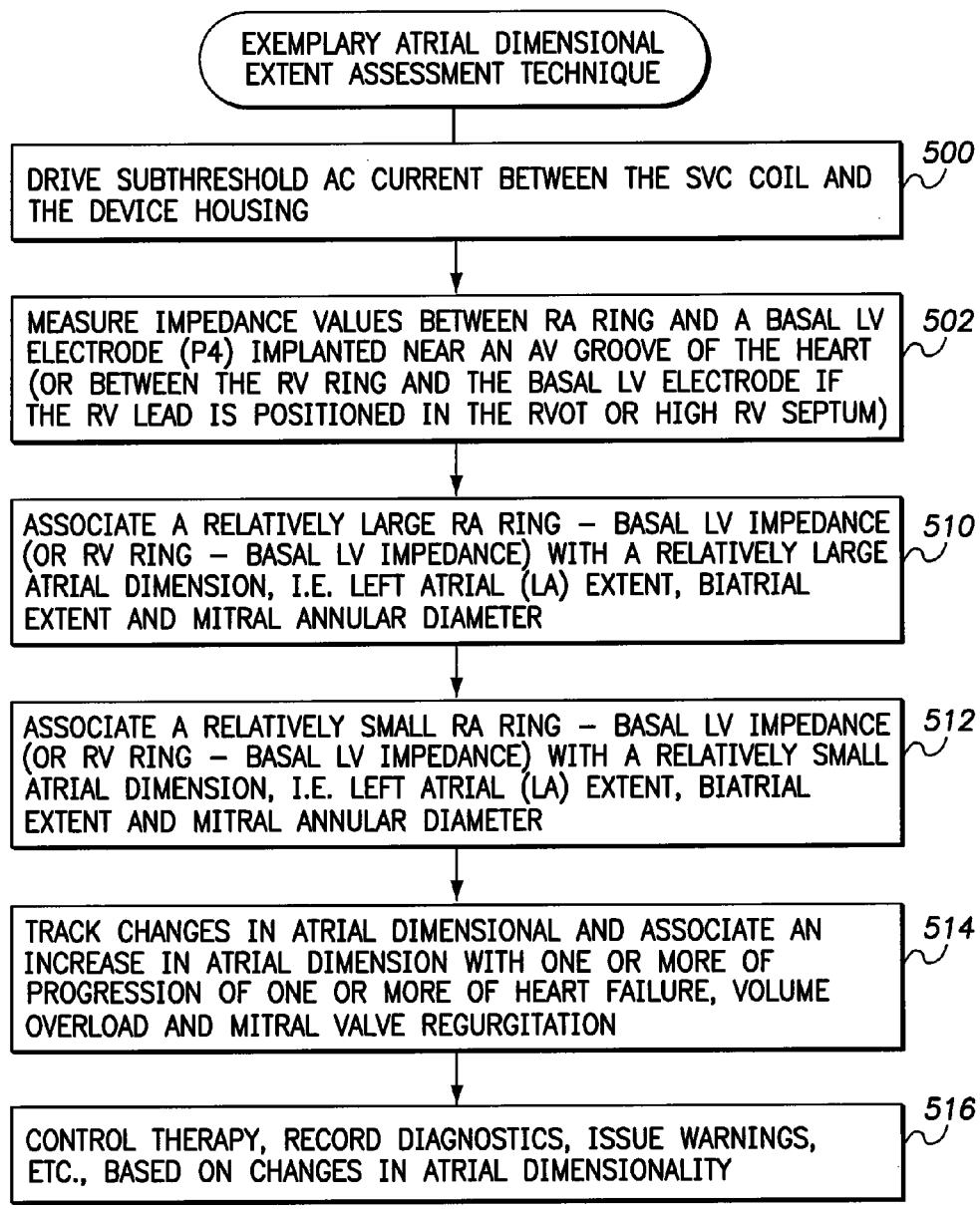
FIG. 10 is a flowchart illustrating an exemplary implementation of the technique of FIG. 2 for assessing atrial extent, wherein an RA ring-basal LV electrode impedance vector is exploited.
Figure 11:
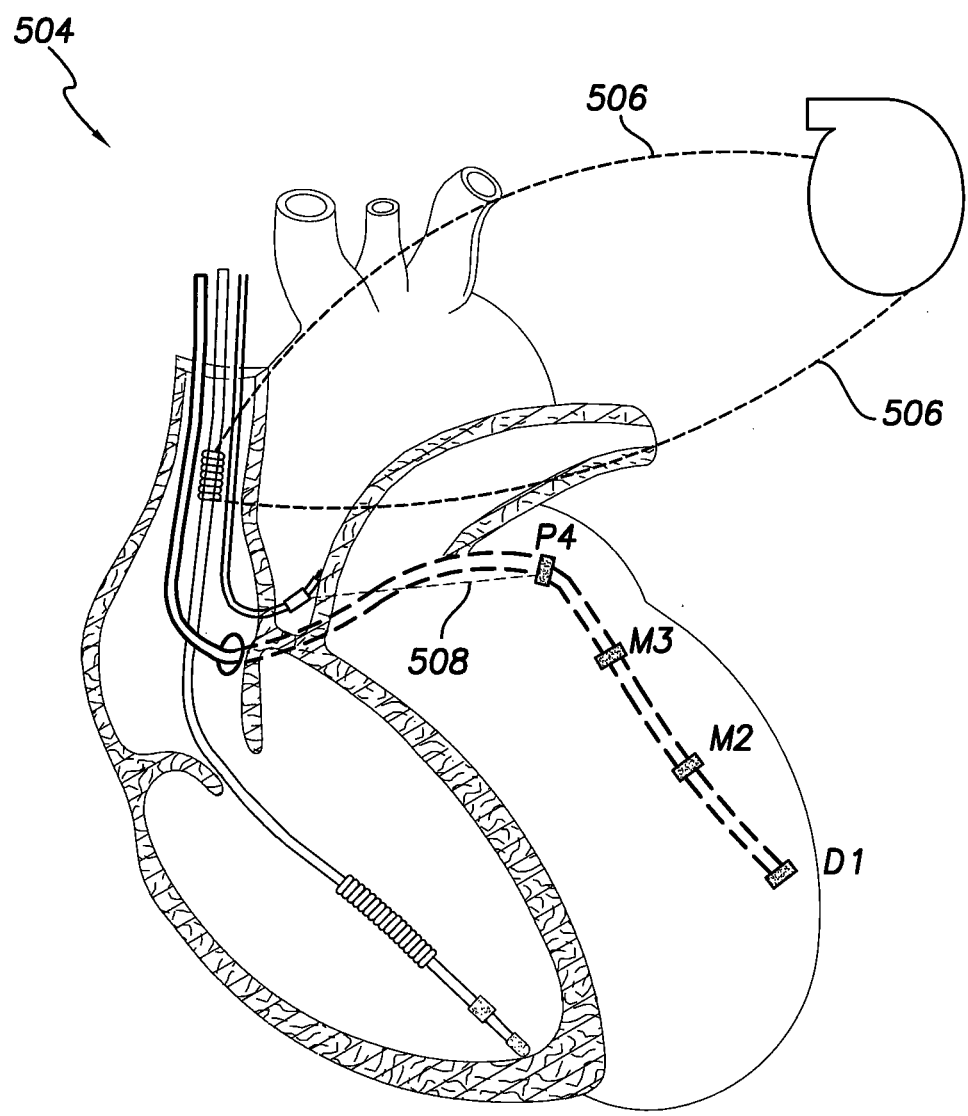
FIG. 11 illustrates the arrangement of electrodes exploited by the technique of FIG. 10 and particularly illustrating the RA ring-basal LV electrode impedance vector.

FIGS. 10 and 11 illustrate techniques that assess atrial dimensional extent using impedance vectors. In a similar manner to the assessment of LV sphericity, it is advantageous to drive current between electrodes that are relatively large and far apart, in order to improve the electric field uniformity at the measurement electrodes. Further, the use of Z0 or PE impedance will be described, but measures of maximum or minimum Zc, peak-to-trough Zc, or any such Zc feature normalized by Z0, may also be used by substituting the opposite direction for interpretation. This method exploits the notion that in many typical configurations for a quadrapole multi-electrode LV lead, the proximal LV electrode P4 will lie in or near the AV groove, allowing a reasonable approximation of the extent of the LA or mitral annulus.

Beginning at step 500 of FIG. 10, the device drives an AC current between the SVC coil and each of the LV electrodes while shorting the LV electrodes. At step 502, the device measures impedance values between the RV ring and the basal LV electrode (P4) implanted near an AV groove of the heart. FIG. 11 illustrates the configuration by way of heart diagram 504. The driving current vector between SVC coil and the device housing is shown by way of lines 506. The RA ring-basal LV impedance vector is shown by way of line 508. Note that, if the RV lead is positioned in the RVOT or high RV septum, the voltage measurement may alternately be taken between RV ring and P4. Returning to FIG. 10, the device at steps 512 and 514 associates a relatively large RA ring-basal LV impedance (or RV ring-basal LV impedance) with a relatively large atrial dimension (i.e. left atrial extent, biatrial extent and mitral annular diameter) and associates a relatively small RA ring-basal LV impedance with a relatively small atrial dimension. More specifically, the impedance computed is interpreted as related to the diameter of left atrium (particularly in the case of a septally positioned RA lead) or as a biatrial dimension. An LA dimension index representative of the atrial extent may be computed from the impedance values. Still further, the index value, or a derived pressure from the dimension, can be input to a multivariate index of overall heart failure progression. Furthermore, the LA dimension index may help improve direct estimates of LA pressure, for example as part of a zLAP algorithm that estimates LAP based in impedance. As with the beneficial changes in LV sphericity discussed above, certain changes in atrial dimension can also be indicative of beneficial or desirable remodeling of the heart.

Note that, since left atrial dimension is closely tied to LAP, any systems or techniques for trending LAP and/or for detecting clinically relevant excursions of LAP can be applied to this LA dimension index to help confirm or refine the index. LAP sensors are discussed in, for example, U.S. Published Patent Application 2003/0055345 of Eigler et al., entitled "Permanently Implantable System and Method for Detecting, Diagnosing and Treating Congestive Heart Failure." Techniques for detecting LAP that do not necessarily require an LAP sensor are discussed in U.S. Provisional Patent Application No. 60/787,884 of Wong et al., entitled, "Tissue Characterization Using Intracardiac Impedances with an Implantable Lead System," filed Mar. 31, 2006, and U.S. patent application Ser. Nos. 11/558,101, 11/557,851, 11/557,870, 11/557,882 and 11/558,088, each entitled "Systems and Methods to Monitor and Treat Heart Failure Conditions", of Panescu et al. See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device." Particularly effective techniques for calibrating impedance-based techniques are set forth in: U.S. patent application Ser. No. 11/559,235, by Panescu et al., entitled "System and Method for Estimating Cardiac Pressure Using Parameters Derived from Impedance Signals Detected by an Implantable Medical Device." See, also, U.S. patent application Ser. No. 11/779,350, by Wenzel et al., filed Jul. 18, 2007, entitled "System and Method for Estimating Cardiac Pressure based on Cardiac Electrical Conduction Delays using an Implantable Medical Device." At least some of these techniques exploit the aforementioned zLAP.

At step 514, the device tracks changes in atrial dimension and associates increases in dimension with one or more of heart failure, volume overload and mitral valve regurgitation. At step 516, the device controls therapy, records diagnostics, issue warnings, etc., based on the progression of heart failure, volume overload and mitral valve regurgitation, as already discussed.

Contact Pressure-Based Confirmation

Assuming the LV lead is in a stable location, after a short time in the body it will become fibrosed in place. As the chamber changes size and shape, the stresses on various portions of the lead body will change. Of particular interest is the contact pressure between the electrodes and the underlying myocardium. As the heart enlarges and becomes more spherical, there should be greater contact pressure between the electrode and tissue. This contact pressure increase may be determined by several ways: a) the pacing impedance may change/decrease over time, b) the evoked response (ER) may change due to different amounts of underlying tissue contributing to the ER signal and/or larger size virtual electrode, c) a pressure or force sensor such as a piezoelectric material may be incorporated into the lead. Regardless of how it is measured, changes in impedance-based dimension or sphericity concordant with changes in contact pressure serve as confirmation that remodeling has occurred.

Figure 12:
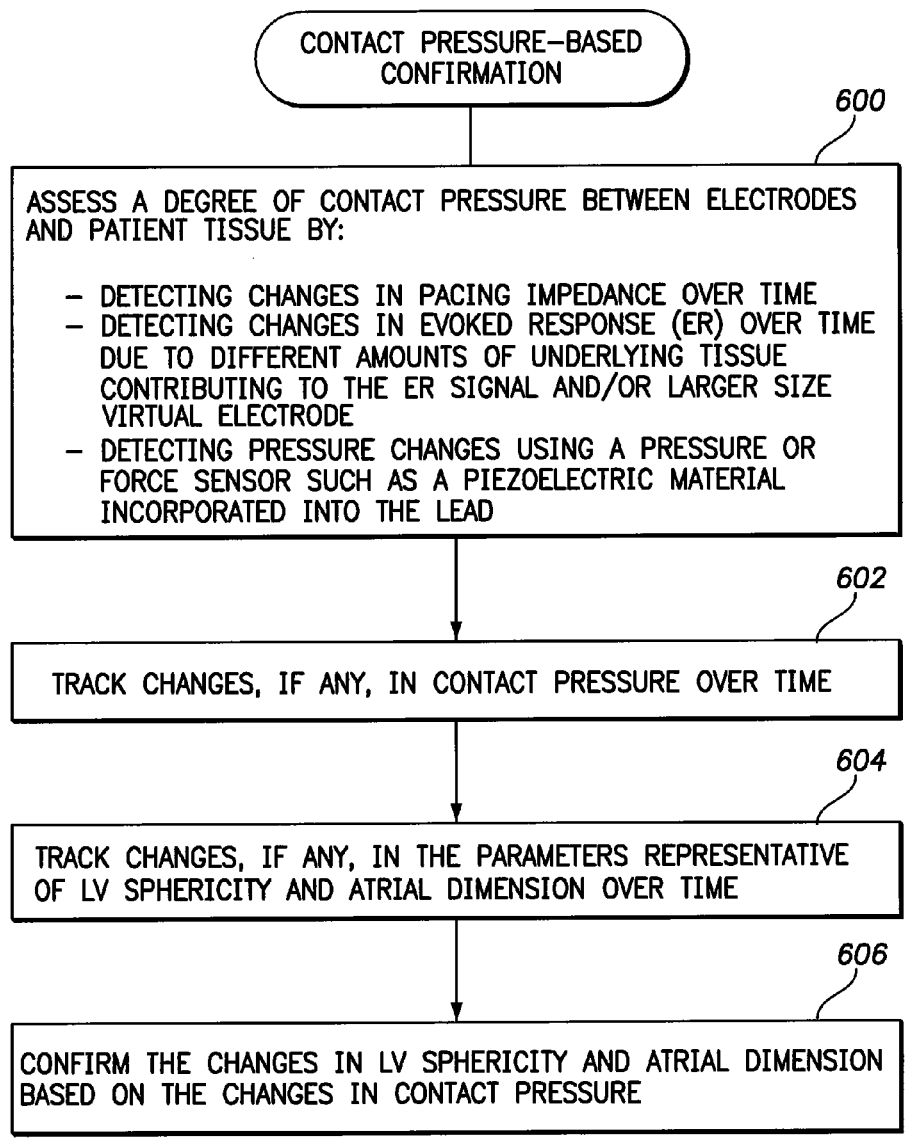
FIG. 12 illustrates techniques for confirming the assessment of LV sphericity and/or atrial extent based on electrode pressure measurements, which may also be performed by the system of FIG. 1.

FIG. 12 summarizes contact-pressure-based confirmation that exploits the foregoing considerations to confirm changes in heart shape. Beginning, at step 600, the device assesses a degree of contact pressure between electrodes and patient tissue by: detecting changes in pacing impedance over time; detecting changes in ER over time; detecting pressure changes using a pressure/force sensor such as a piezoelectric material incorporated into the lead. At step, 602, tracks changes, if any, in contact pressure over time. At step 604, the device tracks changes, if any, in the parameters representative of LV sphericity and atrial dimension over time and, at step 606, the device confirms changes in LV sphericity and atrial dimension based on the changes in contact pressure.

Calibration

It is advantageous with the above methods where impedance is used as a surrogate for dimension, length, diameter, etc., that some calibration be performed. Such calibration is preferably done in a non-invasive manner. For example, transthoracic echocardiography can be used to image the heart. Sonographers then identify the implanted leads and electrodes based on the echogenic reflections they produce. Online analysis of the echo images may be performed to measure various 2-D distances that correspond to inter-electrode distances. The measured distances can be stored in a programmer or in the device memory to serve as calibration factors, thereby scaling impedance in ohms to length in millimeters. Similar measurements could be made using other imaging modalities, including computed tomography (CT), fluoroscopy, magnetic resonance imaging (MRI), etc.

Still further, impedance at the electrode-tissue interface may change over time, possibly resulting in false readings related to impedance-based dimension or sphericity. Accordingly, it may be desirable to use a pacing impedance (as opposed to subthreshold AC current used to obtain the aforementioned impedance measurements) to characterize such changes in underlying substrate, allowing the separation of substrate change and local myocardial/fibrosis remodeling from global chamber remodeling.

Figure 13:
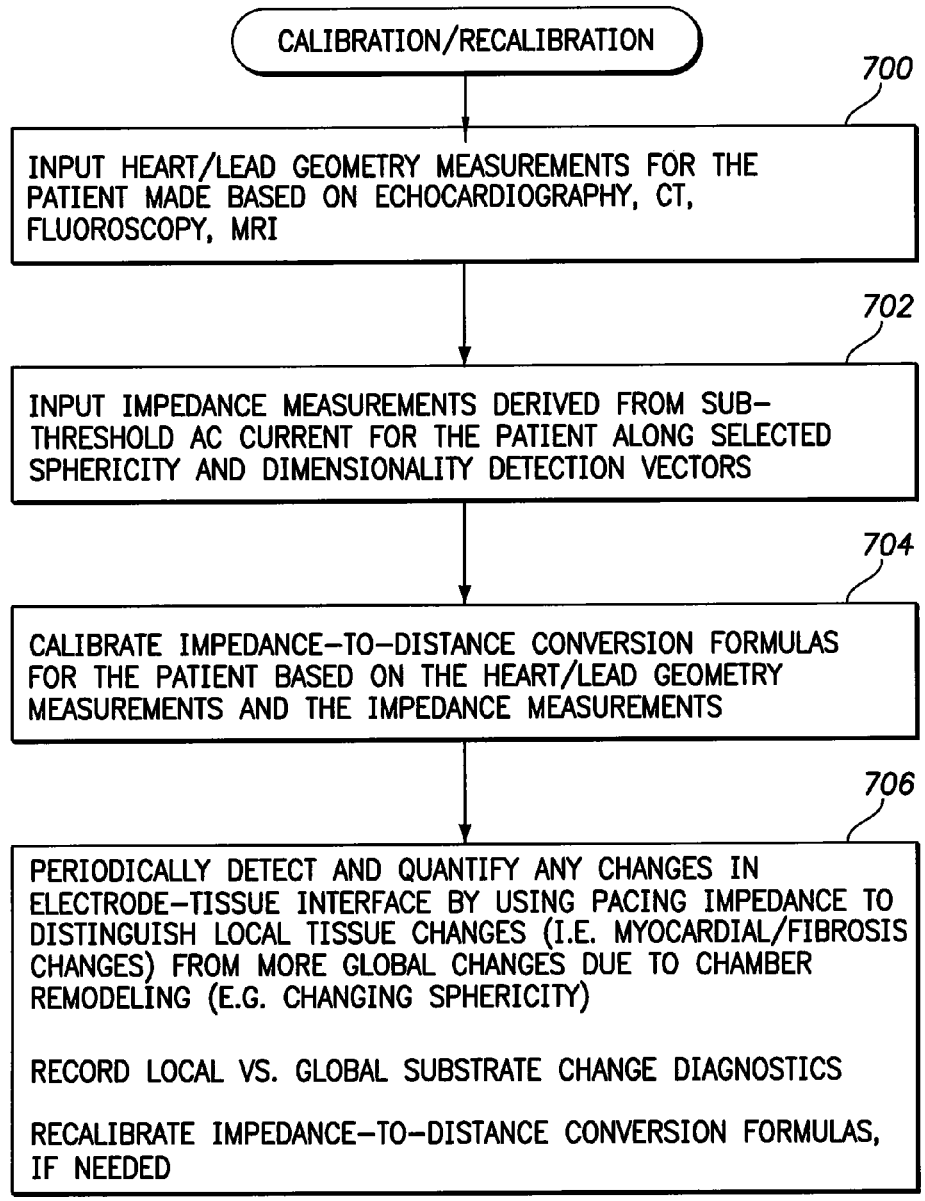
FIG. 13 illustrates calibration/recalibration techniques for calibrating impedance-to-distance conversion formulae used by the system of FIG. 1.

FIG. 13 summarizes calibration/recalibration techniques that may be employed by the pacer/ICD or other systems. At step 700, the device inputs heart/lead geometry measurements for the patient made based on echocardiography, CT, fluoroscopy, MRI or other imaging modalities. At step 702, the device inputs impedance measurements derived from subthreshold AC current for the patient along selected sphericity and dimensional extent detection vectors, such as the aforementioned short-axis and long-axis impedance slices. At step 704, the device then calibrates any impedance-to-distance conversion formulas use by the device for the patient based on the heart/lead geometry measurements and the impedance measurements. As noted, in at least some patients, increasing impedance is associated with increasing interelectrode distances (at least with no change in blood volume, i.e. concentric hypertrophy), whereas increasing chamber volumes with no change or thinning of myocardium (i.e. dilation) typically results in slightly decreased impedance because blood has higher conductivity than myocardium. Accordingly, suitable conversion factors can be determined and updated as needed.

To address possible local changes in the substrate tissue surrounding the electrodes, the device, at step 706, periodically detects and quantifies or otherwise characterizes changes in the electrode-tissue interface by using pacing impedance (rather than subthreshold AC current) to distinguish local tissue changes (i.e. myocardial/fibrosis changes) from more global changes due to chamber remodeling (e.g. changing sphericity). Diagnostic data pertaining to any such local vs. global substrate are recorded. If the changes are significant, it may be appropriate to recalibrate the impedance-to-distance conversion formulas, as these may be affected by local changes.

Techniques and issues pertaining to impedance measurement and calibration are discussed in the following documents: U.S. patent application Ser. No. 11/559,235, filed Nov. 13, 2006, entitled "System and Method for Estimating Cardiac Pressure Using Parameters Derived from Impedance Signals Detected by an Implantable Medical Device"; U.S. Provisional Patent Application No. 60/787,884, filed Mar. 31, 2006 entitled "Tissue Characterization Using Intracardiac Impedances with an Implantable Lead System." See, also, the various "near field"-based impedance assessment techniques described in U.S. patent application Ser. No. 12/853,130, filed Aug. 9, 2010 of Gutfinger et al., entitled "Near Field-Based Systems and Methods for Assessing Impedance and Admittance for use by an Implantable Medical Device" and in U.S. patent application Ser. No. 12/853,157, also filed Aug. 9, 2010 of Gutfinger et al., entitled "Systems and Methods for Estimating Left Atrial Pressure (LAP) in Patients with Acute Mitral Valve Regurgitation for use by an Implantable Medical Device." See, also, U.S. patent application Ser. No. 12/109,304, of also Gutfinger et al., entitled "System and Method for Calibrating Cardiac Pressure Measurements Derived from Signals Detected by an Implantable Medical Device."

What have been described in FIGS. 1-13 are various exemplary systems and techniques for assessing heart chamber sphericity and dimensional extent based on impedance or related signals. Although primarily described with respect to examples having a pacer/ICD, other implantable medical devices may be equipped to exploit the techniques described herein such as CRT devices and CRT-D devices (i.e. a CRT device also equipped to deliver defibrillation shocks) or CRT-P devices (i.e. a CRT device also equipped to deliver pacing.) For the sake of completeness, an exemplary pacer/ICD with CRT capability will now be described, which includes components for performing at least some of the functions and steps already described.

Exemplary Pacer/ICD

Figure 14:
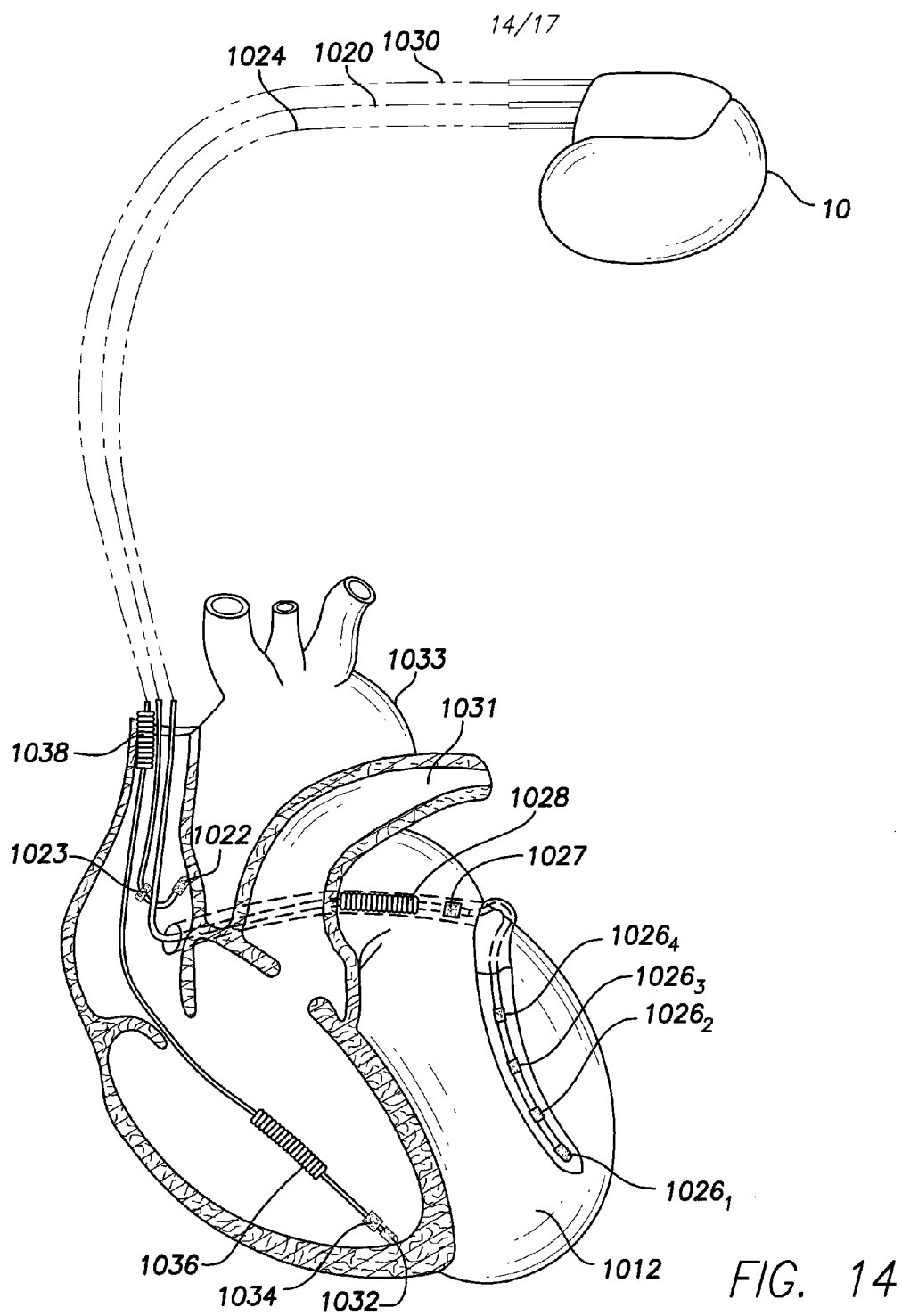
FIG. 14 is a simplified, partly cutaway view, illustrating the implantable device of FIG. 1 along with at set of leads implanted into the heart of the patient.
Figure 15:
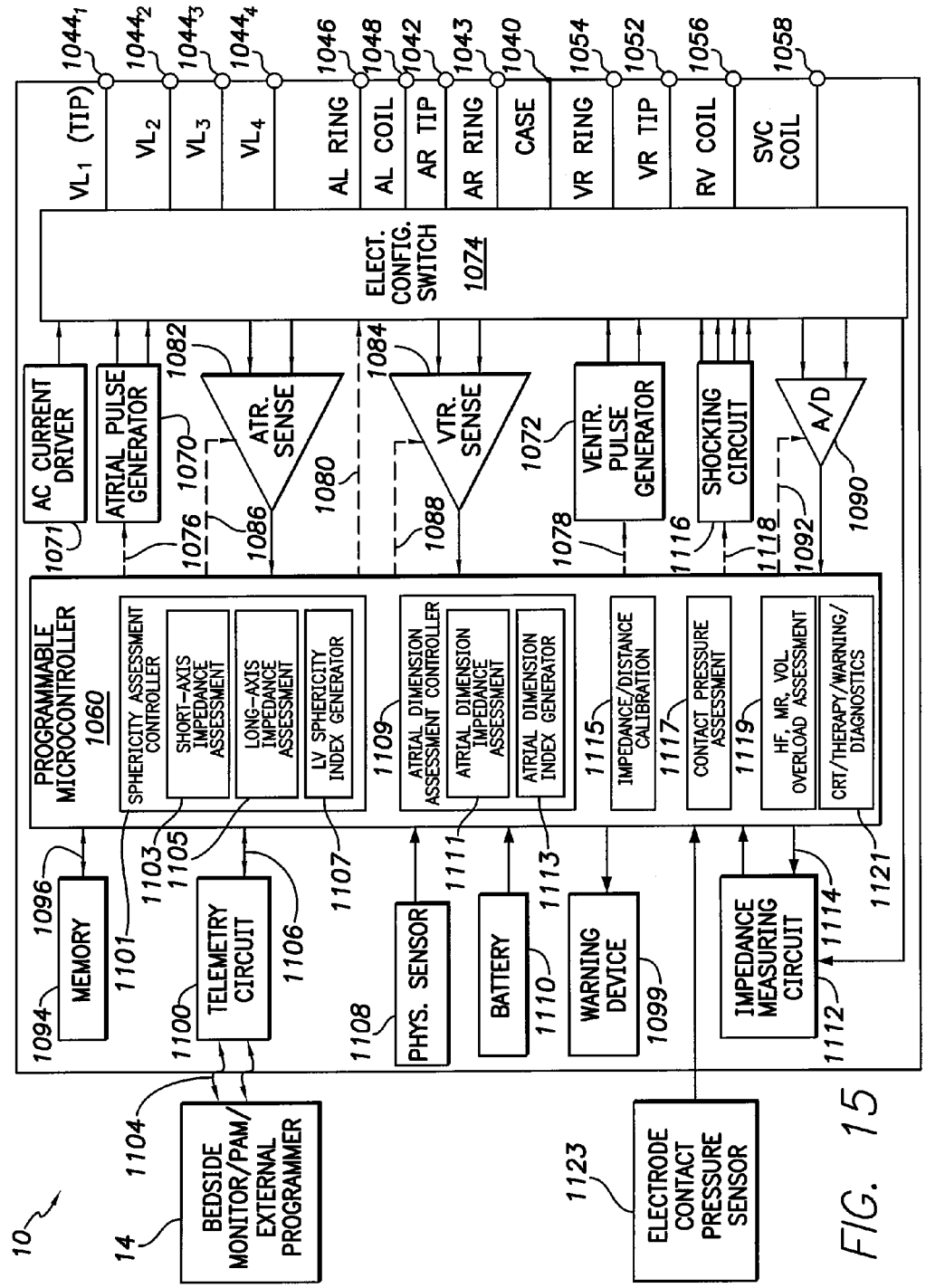
FIG. 15 is a functional block diagram of the pacer/ICD of FIG. 14, illustrating basic circuit elements that provide cardioversion, defibrillation and/or pacing stimulation in the heart, particularly illustrating ob-board assessment components for use with the techniques of FIGS. 2-14.

With reference to FIGS. 14 and 15, a description of an exemplary pacer/ICD will now be provided. FIG. 14 provides a simplified block diagram of the pacer/ICD, which is a dual-chamber stimulation device capable of treating both fast and slow arrhythmias with stimulation therapy, including cardioversion, defibrillation, and pacing stimulation, and also capable of assessing chamber sphericity and dimension, as discussed above. To provide other atrial chamber pacing stimulation and sensing, pacer/ICD 10 is shown in electrical communication with a heart 1012 by way of a left atrial lead 1020 having an atrial tip electrode 1022 and an atrial ring electrode 1023 implanted in the atrial appendage. Pacer/ICD 10 is also in electrical communication with the heart by way of a right ventricular lead 1030 having, in this embodiment, a ventricular tip electrode 1032, a right ventricular ring electrode 1034, a right ventricular (RV) coil electrode 1036, and a superior vena cava (SVC) coil electrode 1038. Typically, the right ventricular lead 1030 is transvenously inserted into the heart so as to place the RV coil electrode 1036 in the right ventricular apex, and the SVC coil electrode 1038 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a multi-pole LV lead 1024 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 1024 is designed to receive atrial and ventricular cardiac signals and to deliver left ventricular pacing therapy using a set of four left ventricular electrodes $1026_1$, $1026_2$, $1026_3$, and $1026_4$ (thereby providing a quadrapole lead), left atrial pacing therapy using at least a left atrial ring electrode 1027, and shocking therapy using at least a left atrial coil electrode 1028. The $1026_1$ LV electrode may also be referred to as a "tip" or "distal" LV electrode. The $1026_4$ LV electrode may also be referred to as a "proximal" LV electrode. In other examples, more or fewer LV electrodes are provided. Although only three leads are shown in FIG. 14, it should also be understood that additional leads (with one or more pacing, sensing and/or shocking electrodes) might be used and/or additional electrodes might be provided on the leads already shown, such as additional electrodes on the RV lead. Also note that the locations of the LV electrodes are merely exemplary. Preferred locations of the electrodes is discussed above and shown in some of the other figures. For example, as already explained, the most proximal of the LV electrodes is positioned, in at least some embodiments, in or near the AV groove.

A simplified block diagram of internal components of pacer/ICD 10 is shown in FIG. 15. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 1040 for pacer/ICD 10, shown schematically in FIG. 15, is often referred to as the "can", "case" or "case electrode" and may be programmably selected to act as the return electrode for all "unipolar" modes. The housing 1040 may further be used as a return electrode alone or in combination with one or more of the coil electrodes, 1028, 1036 and 1038, for shocking purposes. The housing 1040 further includes a connector (not shown) having a plurality of terminals, 1042, 1043, $1044_1$-$1044_4$, 1046, 1048, 1052, 1054, 1056 and 1058 (shown schematically and, for convenience, the names of the electrodes to which they are connected are shown next to the terminals). As such, to achieve right atrial sensing and pacing, the connector includes at least a right atrial tip terminal ($A_R$ TIP) 1042 adapted for connection to the atrial tip electrode 1022 and a right atrial ring ($A_R$ RING) electrode 1043 adapted for connection to right atrial ring electrode 1023. To achieve left chamber sensing, pacing and shocking, the connector includes a left ventricular tip terminal ($VL_1$ TIP) $1044_1$ and additional LV electrode terminals $1044_2$. $1044_4$ for the other LV electrodes of the quadrapole LV lead.

The connector also includes a left atrial ring terminal ($A_L$ RING) 1046 and a left atrial shocking terminal ($A_L$ COIL) 1048, which are adapted for connection to the left atrial ring electrode 1027 and the left atrial coil electrode 1028, respectively. To support right chamber sensing, pacing and shocking, the connector further includes a right ventricular tip terminal ($V_R$ TIP) 1052, a right ventricular ring terminal ($V_R$ RING) 1054, a right ventricular shocking terminal ($V_R$ COIL) 1056, and an SVC shocking terminal (SVC COIL) 1058, which are adapted for connection to the right ventricular tip electrode 1032, right ventricular ring electrode 1034, the $V_R$ coil electrode 1036, and the SVC coil electrode 1038, respectively.

At the core of pacer/ICD 10 is a programmable microcontroller 1060, which controls the various modes of stimulation therapy. As is well known in the art, the microcontroller 1060 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 1060 includes the ability to process or monitor input signals (data) as controlled by a program code stored in a designated block of memory. The details of the design and operation of the microcontroller 1060 are not critical to the invention. Rather, any suitable microcontroller 1060 may be used that carries out the functions described herein. The use of microprocessor-based control circuits for performing timing and data analysis functions are well known in the art.

As shown in FIG. 15, an atrial pulse generator 1070 and a ventricular pulse generator 1072 generate pacing stimulation pulses for delivery by the right atrial lead 1020, the right ventricular lead 1030, and/or the LV lead 1024 via an electrode configuration switch 1074. It is understood that in order to provide stimulation therapy in each of the four chambers of the heart, the atrial and ventricular pulse generators, 1070 and 1072, may include dedicated, independent pulse generators, multiplexed pulse generators or shared pulse generators. The pulse generators, 1070 and 1072, are controlled by the microcontroller 1060 via appropriate control signals, 1076 and 1078, respectively, to trigger or inhibit the stimulation pulses. Additionally, an AC current driver circuit 1071 is shown that controls the generation of subthreshold AC current for use in generating a current field for measuring impedance. In other implementations, this AC current might instead be generated by the impedance measuring circuit 1112, discussed below.

The microcontroller 1060 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 1074 includes a plurality of switches for connecting the desired electrodes to the appropriate I/O circuits, thereby providing complete electrode programmability. Accordingly, the switch 1074, in response to a control signal 1080 from the microcontroller 1060, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 1082 and ventricular sensing circuits 1084 may also be selectively coupled to the right atrial lead 1020, LV lead 1024, and the right ventricular lead 1030, through the switch 1074 for detecting the presence of cardiac activity in each of the four chambers of the heart. Accordingly, the atrial and ventricular sensing circuits 1082, 1084 may include dedicated sense amplifiers, multiplexed amplifiers or shared amplifiers. The switch 1074 determines the "sensing polarity" of the cardiac signal by selectively closing the appropriate switches, as is also known in the art. In this way, the clinician may program the sensing polarity independent of the stimulation polarity. Each sensing circuit 1082, 1084 preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits 1082, 1084 are connected to the microcontroller 1060 which, in turn, are able to trigger or inhibit the atrial and ventricular pulse generators 1070, 1072 respectively, in a demand fashion in response to the absence or presence of cardiac activity in the appropriate chambers of the heart.

For arrhythmia detection, pacer/ICD 10 utilizes the atrial and ventricular sensing circuits 1082, 1084 to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 1060 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 1090. The data acquisition system 1090 is configured to acquire intracardiac electrogram signals, convert the raw analog data into a digital signal, and store the digital signals for later processing and/or telemetric transmission to an external device 1102. The data acquisition system 1090 is coupled to the right atrial lead 1020, the LV lead 1024, and the right ventricular lead 1030 through the switch 1074 to sample cardiac signals across any pair of desired electrodes. The microcontroller 1060 is further coupled to a memory 1094 by a suitable data/address bus 1096, wherein the programmable operating parameters used by the microcontroller 1060 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 1094 through a telemetry circuit 1100 in telemetric communication with the external device 1102, such as a programmer, transtelephonic transceiver or a diagnostic system analyzer. The telemetry circuit 1100 is activated by the microcontroller by a control signal 1106. The telemetry circuit 1100 advantageously allows intracardiac electrograms and status information relating to the operation of pacer/ICD 10 (as contained in the microcontroller 1060 or memory 1094) to be sent to the external device 1102 through an established communication link 1104. Pacer/ICD 10 further includes an accelerometer or other physiologic sensor 1108, commonly referred to as a "rate-responsive" sensor because it is typically used to adjust pacing stimulation rate according to the exercise state of the patient. However, the physiological sensor 1108 may further be used to detect changes in cardiac output, changes in the physiological condition of the heart, or diurnal changes in activity (e.g., detecting sleep and wake states) and to detect arousal from sleep. Accordingly, the microcontroller 1060 responds by adjusting the various pacing parameters (such as rate, AV delay, W delay, etc.) at which the atrial and ventricular pulse generators, 1070 and 1072, generate stimulation pulses. While shown as being included within pacer/ICD 10, it is to be understood that the physiologic sensor 1108 may also be external to pacer/ICD 10, yet still be implanted within or carried by the patient. A common type of rate responsive sensor is an activity sensor incorporating an accelerometer or a piezoelectric crystal, which is mounted within the housing 1040 of pacer/ICD 10. Other types of physiologic sensors are also known, for example, sensors that sense the oxygen content of blood, respiration rate and/or minute ventilation, pH of blood, ventricular gradient, LAP, etc.

The pacer/ICD additionally includes a battery 1110, which provides operating power to all of the circuits shown in FIG. 15. The battery 1110 may vary depending on the capabilities of pacer/ICD 10. If the system only provides low voltage therapy, a lithium iodine or lithium copper fluoride cell typically may be utilized. For pacer/ICD 10, which employs shocking therapy, the battery 1110 should be capable of operating at low current drains for long periods, and then be capable of providing high-current pulses (for capacitor charging) when the patient requires a shock pulse. The battery 1110 should also have a predictable discharge characteristic so that elective replacement time can be detected. Accordingly, appropriate batteries are employed.

As further shown in FIG. 15, pacer/ICD 10 is shown as having an impedance measuring circuit 1112, which is enabled by the microcontroller 1060 via a control signal 1114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; detecting the opening of heart valves, and measuring values useful for assessing current drain and device longevity, etc. The impedance measuring circuit 1112 is advantageously coupled to the switch 1174 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 1060 further controls a shocking circuit 1116 by way of a control signal 1118. The shocking circuit 1116 generates shocking pulses of low (up to 0.5 joules), moderate (0.5-10 joules) or high energy (11 to 40 joules or more), as controlled by the microcontroller 1060. Such shocking pulses are applied to the heart of the patient through at least two shocking electrodes, and as shown in this embodiment, selected from the left atrial coil electrode 1028, the RV coil electrode 1036, and/or the SVC coil electrode 1038. The housing 1040 may act as an active electrode in combination with the RV electrode 1036, or as part of a split electrical vector using the SVC coil electrode 1038 or the left atrial coil electrode 1028 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 1060 is capable of controlling the synchronous or asynchronous delivery of the shocking pulses.

An internal warning device 1099 may be provided for generating perceptible warning signals to the patient via vibration, voltage or other methods.

Insofar as sphericity/dimensional extent is concerned, the microcontroller includes an on-board sphericity assessment controller 1101, which performs or controls the various sphericity assessment functions discussed above. The sphericity controller includes a short-axis impedance assessment system 1103, a long-axis impedance assessment system 1105 and an LV sphericity index or score generator 1107, which operate based in impedance data received from the impedance measuring circuit 1112. The microcontroller also includes an on-board atrial dimension assessment controller 1109, which performs or controls the various atrial dimension assessment functions discussed above. The dimension controller includes an atrial-dimension-impedance-assessment system 1111 and an atrial dimension index or score generator 1113, which operate based in impedance data received from the impedance measuring circuit. Additionally, the microcontroller includes an impedance/distance calibration system 1115 for calibrating any impedance to distance conversions that might be performed by the device. As noted, calibration may rely on echocardiography data provided by an external system. The calibration system also assesses local vs. global changes in tissue substrate, as described above. A contact-pressure-assessment system 1117 assesses contact pressure, as discussed above. An electrode contract pressure sensor 1123 may be provided on one or more electrodes (such as a piezoelectric device) to detect contact pressure.

A heart failure, MR, LV volume-overload-assessment system 1119 detects heart failure, MR, LV volume overload or other related conditions based on the various indices or scores generated by the device and tracks progression of such conditions. Therapy (including CRT), warnings and/or diagnostics are generated and/or controlled by a therapy/warning/diagnostics controller 1121, which operates in conjunction with warning device 1099 and memory 1094. Note that, in examples wherein sphericity/dimensional extent assessment is fully controlled by an external device, the implantable device need not include each of these on-board components.

Note also that, depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein can be performed by (or under the control of) an external device. For the sake of completeness, a detailed description of an exemplary device programmer will now be provided.

Exemplary External Programmer

Figure 16:
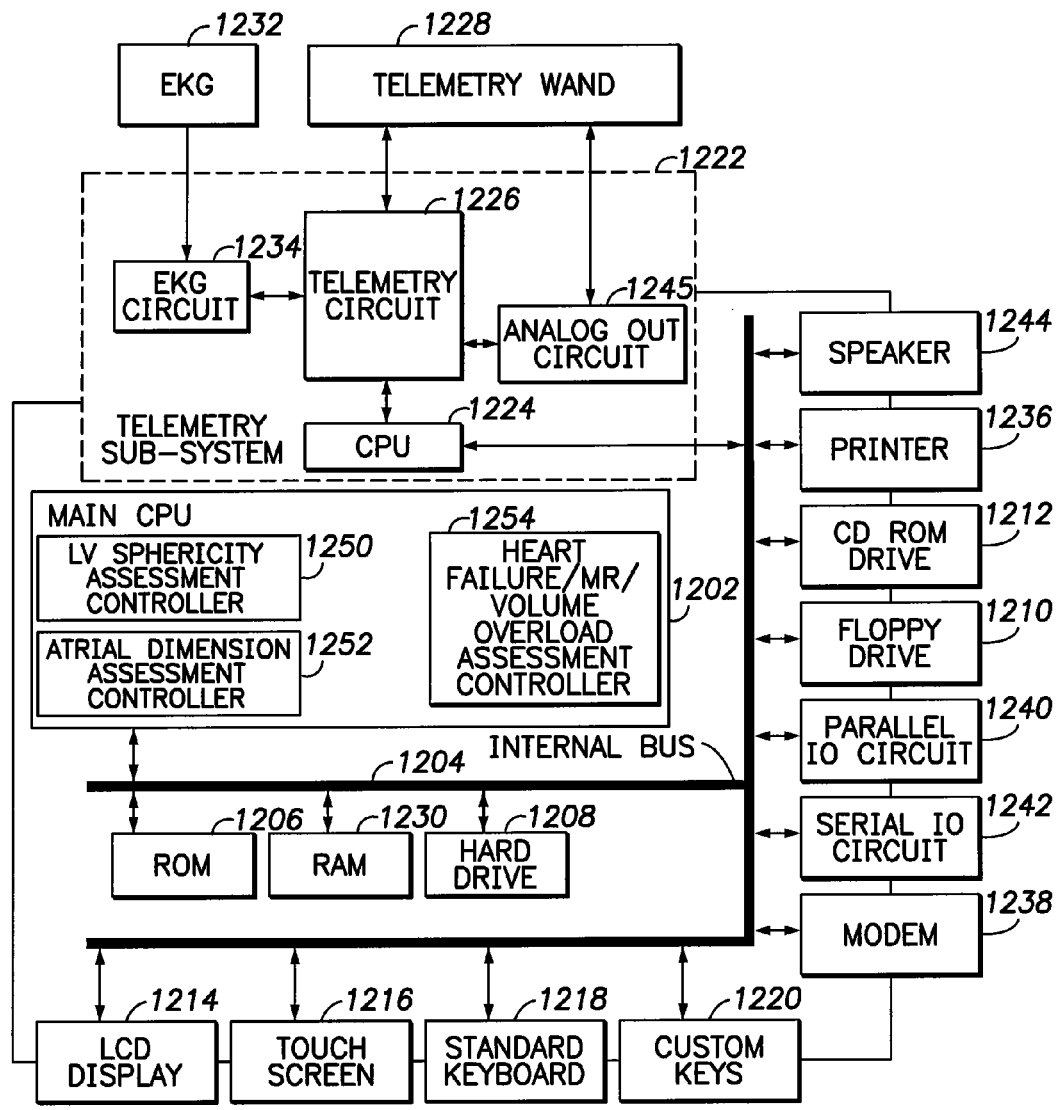
FIG. 16 is a functional block diagram illustrating components of the external device programmer of FIG. 1, particularly illustrating programmer-based assessment systems for performing/controlling the techniques of FIGS. 2-14.

FIG. 16 illustrates pertinent components of an external programmer 14 for use in programming the pacer/ICD of FIGS. 14 and 15 and for performing the above-described optimization techniques. For completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 1202, which may be a generally programmable microprocessor or microcontroller or may be a dedicated processing device such as an application specific integrated circuit (ASIC) or the like. Software instructions to be performed by the CPU are accessed via an internal bus 1204 from a read only memory (ROM) 1206 and random access memory 1230. Additional software may be accessed from a hard drive 1208, floppy drive 1210, and CD ROM drive 1212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 1214 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 1216 overlaid on the LCD display or through a standard keyboard 1218 supplemented by additional custom keys 1220, such as an emergency VVI (EVVI) key. The EVVI key sets the implanted device to a safe WI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 1202 transmits appropriate signals to a telemetry subsystem 1222, which provides components for directly interfacing with the implanted devices, and the EKG leads. Telemetry subsystem 1222 includes its own separate CPU 1224 for coordinating the operations of the telemetry subsystem. Main CPU 1202 of programmer communicates with telemetry subsystem CPU 1224 via internal bus 1204. Telemetry subsystem additionally includes a telemetry circuit 1226 connected to telemetry wand 1228, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 1234 for receiving surface EKG signals from a surface EKG system 1232. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 1230, hard drive 1208 or within a floppy diskette placed within floppy drive 1210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 1222 receives EKG signals from EKG leads 1232 via an EKG processing circuit 1234. As with data retrieved from the implanted device itself, signals received from the EKG leads are stored within one or more of the storage devices of the external programmer. Typically, EKG leads output analog electrical signals representative of the EKG. Accordingly, EKG circuit 1234 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 1202, the programming commands are converted to specific programmable parameters for transmission to the implanted devices via telemetry wand 1228 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 1236.

Programmer/monitor 14 also includes an internet connection component 1238 to permit direct transmission of data to other programmers via the public switched telephone network (PSTN) or other interconnection line, such as a T1 line or fiber optic cable or via wireless systems. Depending upon the implementation, the internet connection component may be connected directly to internal bus 1204 may be connected to the internal bus via either a parallel port 1240 or a serial port 1242. Other peripheral devices may be connected to the external programmer via parallel port 1240 or a serial port 1242 as well. Although one of each is shown, a plurality of input output (IO) ports might be provided. A speaker 1244 is included for providing audible tones to the user, such as a warning beep in the event improper input is provided by the physician. Telemetry subsystem 1222 additionally includes an analog output circuit 1245 for controlling the transmission of analog output signals, such as IEGM signals output to an EKG machine or chart recorder.

Insofar as sphericity/dimensional extent assessment is concerned, main CPU 1202 includes an LV sphericity assessment controller 1250 and an atrial dimension assessment controller 1252, which operate based on impedance data or other data received from the implanted device to perform the assessment techniques discussed above, including generating and interpreting indices or scores. A heart failure, MR, volume-overload-assessment controller 1254 detects heart failure, MR, LV volume overload or other related conditions within the patient based on the various indices or scores and tracks progression of such conditions. In response to the detection of any such conditions, the programmer can transmit commands to reprogram the device to deliver suitable therapy, such as CRT, subject to the control of the clinician. Note that if the pacer/ICD has on-board assessment components (as shown in FIG. 15), then the assessment controllers of the external device may be equipped to operate in conjunction with the on-board components to supplement or confirm any assessment made by the on-board components.

Depending upon the implementation, the various components of the CPU may be implemented as separate software modules or the modules may be combined to permit a single module to perform multiple functions. In addition, although shown as being components of the CPU, some or all of these components may be implemented separately, using ASICs or the like.

With the programmer configured as shown, a clinician or other user operating the external programmer is capable of retrieving, processing and displaying a wide range of information received from the implanted device and to reprogram the implanted device if needed. The descriptions provided herein with respect to FIG. 15 are intended merely to provide an overview of the operation of programmer and are not intended to describe in detail every feature of the hardware and software of the programmer and is not intended to provide an exhaustive list of the functions performed by the programmer.

Figure 17:
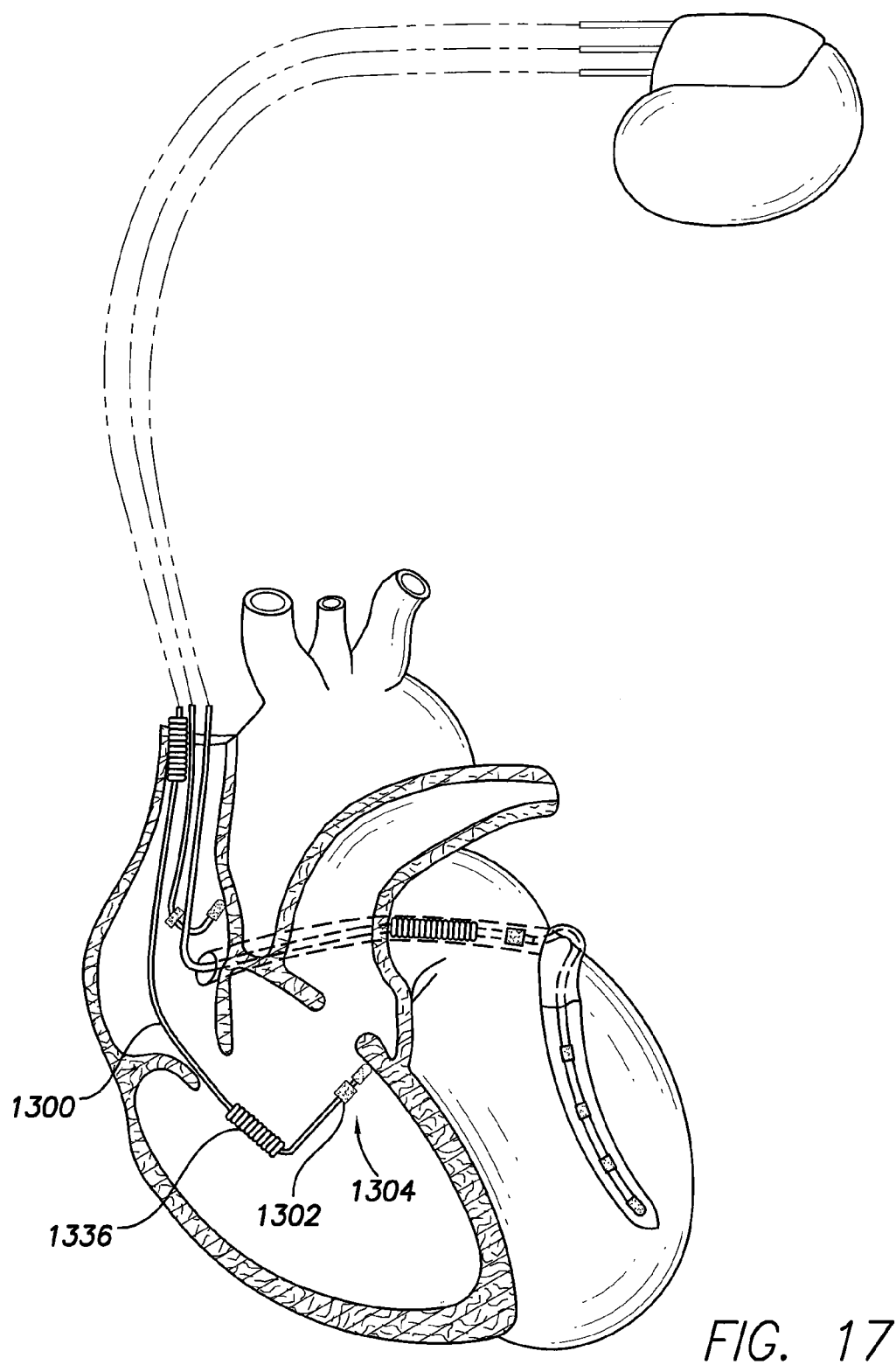
FIG. 17 is a simplified, partly cutaway view, illustrating the implantable device of FIG. 1 along with a set of leads implanted into the heart of the patient including an RVOT lead.

Finally, for the sake of completeness, an RVOT lead is illustrated, which is employed in at least some of the implementation discussed above RVOT Lead FIG. 17 illustrates an RVOT lead 1300 implanted through the RA into the RV. A tip of the RVOT lead is affixed in or near the RVOT 1304 of the heart of the patient. The RVOT lead can include one or more electrodes. An RVOT ring electrode 1302 is specifically identified. Also, as shown, the RVOT lead can include an RV coil 1306.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient, the method comprising:
   taking a first measurement of the impedance between an electrode of a first lead and a first of a plurality of electrodes of a second lead and taking a first measurement of the impedance between the electrode of the first lead and a second of a plurality of electrodes the second lead, with a portion of the first lead being implanted within the right ventricle of the heart of the patient and a proximal end of the first lead being connected to the implantable medical device, and a portion of the second lead being implanted at least proximate the left ventricle of the heart of the patient, and a proximal end of the second lead being connected to the implantable medical device;

taking, at a time subsequent to the step of taking the first measurement, a second measurement of the impedance between the electrode of the first lead and the first of a plurality of electrodes of the second lead, and taking, at a time subsequent to the step of taking the first measurement, a second measurement of the impedance between the electrode of the first lead and the second of a plurality of electrodes of the second lead;

determining, if any, change in impedance from the first measured impedance and the second measure impedance that was taken between the electrode of the first lead and the first of a plurality of electrodes of the second lead, and if a change is determined, tracking the change of impedance between the electrode of the first lead and the first of a plurality of electrodes of the second lead;

determining, if any, change in impedance from the first measured impedance and the second measure impedance that was taken between the electrode of the first lead and the second of a plurality of electrodes of the second lead, and if a change is determined, tracking the change of the impedance between the electrode of the first lead and the second of a plurality of electrodes of the second lead;

repeating at least one time both of the steps of taking impedance measurements and the steps of determining change in impedance; and if changes are tracked, tracking the progression of the shape of the left ventricular chamber of the patient between an ellipsoid shape and a spherical shape based upon the tracked change of impedance measurements, and controlling at least one of a plurality of functions of the implantable medical device within the patient based upon the tracked progression of the shape of the left ventricular chamber.

2. The method of claim 1, and further comprising driving a current between the electrode of the first lead and a device housing of the implantable medical device; and measuring the electrical impedance between the electrode of the first lead and the device housing.

3. The method of claim 2 wherein the electrode of the first lead is a right ventricular coil electrode.

4. The method of claim 2 wherein both steps of taking measurements of impedance are based on voltage drops between the electrode of the first lead and the respective plurality of electrodes of the second lead.

5. The method of claim 2 further including:
tracking the progression of change in the left ventricular sphericity of the heart of the patient over time.

6. The method of claim 2 further including:
determining a score representative of left ventricular ellipsoidicity versus left ventricular sphericity based on the measured electrical impedances and tracking the score over time.

7. The method of claim 6 wherein the score incorporates a comparison of one or more of the measured electrical impedances to a means of the measured electrical impedances.

8. The method of claim 2 wherein the plurality of electrodes of the second lead include an apical left ventricular electrode, a basal left ventricular electrode and a set of intermediate left ventricular electrodes and wherein determining the changes in the left ventricular sphericity includes:

determining distances between the plurality of electrodes of the second lead and the electrode of the first lead based on the impedance values and sorting from basal to apical; and assessing the left ventricular sphericity based on whether there are changes in the distances from basal to apical.

9. The method of claim 8 wherein assessing the left ventricular sphericity based on the distances from basal to apical includes:

detecting deviations in the distances from basal to apical;

generating a sphericity index by incrementing points for each decrease in distance when stepping from basal to apical and decrementing points for each increase when stepping from basal to apical; and assessing sphericity based on the sphericity index.

10. The method of claim 9 further including:
tracking changes, if any, in the sphericity index over time; and associating an increase in the sphericity index with progression of one or more of heart failure, volume overload and mitral regurgitation.

11. The method of claim 8 further including:
measuring separate impedance values between the right atrial electrode and each of the plurality of electrodes of the second lead.

12. The method of claim 11 wherein assessing the left ventricular sphericity further includes:

determining a ratio of the measured impedances between the electrode of the first lead and each of the of the plurality of electrodes of the second lead to the measured impedances between the right atrial electrode and each of the plurality of electrodes of the second lead;

determining whether the ratios decrease from the basal electrode to the apical electrode and, based upon this determination assessing the amount of change in the left ventricular sphericity.

13. The method of claim 1 wherein the implantable medical device is connected to a lead system having right ventricular (RV) lead positioned in an RV outflow tract (RVOT) with an RV coil electrode, and a set of multi-electrode left ventricular (multi-electrode LV) electrodes including a basal LV electrode implanted near an atrioventricular (AV) groove of the heart of the patient, and wherein measuring parameters representative of impedance includes:

driving current between the RVOT coil electrode and a device housing electrode; and measuring RVOT coil-basal LV impedance between the RVOT coil and the basal LV electrode.

14. The method of claim 13 and further comprising determining dimensional extent wherein determining parameters representative of dimensional extent includes:

associating a first RVOT coil-basal LV impedance with an atrial extent of a first size; and associating a second RVOT coil-basal LV impedance, the second RVOT coil-basal LV impedance being less than the first, with an atrial extend of a second size, with the second size being smaller that the first size.

15. The method of claim 14 further including:
calculating an index associated with atrial dimensional extent;

tracking the atrial dimensional extent index over time; and associating an increase in the atrial dimensional extent index with progression of heart failure.

16. The method of claim 15 including a preliminary step of calibrating an impedance-to-distance conversion procedure and wherein determining parameters representative of one or more of heart chamber sphericity and dimensional extent includes determining distance values associated with sphericity and dimension.

17. The method of claim 14 wherein the device is connected to a lead system having a set of electrodes and where the method further inclu'des:
- assessing a degree of contact pressure between the electrodes and patient tissue; and
- tracking changes, if any, in contact pressure over time.

18. The method of claim 17 further including:
- tracking changes, if any, in the parameters representative of sphericity and dimensional extent over time based on impedance measurements; and
- confirming the changes in sphericity and dimensional extent based on the changes in contact pressure.

19. The method of claim 17 further including:
- delivering pacing pulses;
- detecting impedance values based on pacing impedance measurements;
- detecting tissue substrate parameters representative of changes, if any, in an electrode tissue interface based on the impedance values; and
- distinguishing local tissue changes from changes due to global cardiac remodeling from the tissue substrate parameters.

20. The method of claim 1 wherein controlling at least one device function includes controlling therapy based on the changes in the left ventricular sphericity.

21. The method of claim 1 wherein at least some of the steps are performed by the device itself.

22. The method of claim 1 wherein the steps of measuring impedance includes measuring at least one of impedance, admittance, conductance and immittance.

* * * * *